United States Patent
Sultan et al.

(10) Patent No.: US 11,807,789 B2
(45) Date of Patent: Nov. 7, 2023

(54) METHOD OF INHIBITING CARBON DIOXIDE HYDRATE FORMATION

(71) Applicant: King Fahd University of Petroleum and Minerals, Dhahran (SA)

(72) Inventors: Abdullah S. Sultan, Dhahran (SA); Tinku Saikia, Dhahran (SA); Jaber Al Jaberi, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 111 days.

(21) Appl. No.: 17/704,339

(22) Filed: Mar. 25, 2022

(65) Prior Publication Data

US 2023/0303920 A1 Sep. 28, 2023

(51) Int. Cl.
*E21B 41/06* (2006.01)
*C09K 11/07* (2006.01)
(Continued)

(52) U.S. Cl.
CPC .............. *C09K 11/07* (2013.01); *C07C 29/76* (2013.01); *E21B 41/0064* (2013.01);
(Continued)

(58) Field of Classification Search
None
See application file for complete search history.

(56) References Cited

U.S. PATENT DOCUMENTS

| 9,328,283 B2 | 5/2016 | Barr |
| 9,416,330 B2 | 8/2016 | Titley |

(Continued)

FOREIGN PATENT DOCUMENTS

| IN | 201831022071 | | 12/2019 |
| KR | 20200055276 A | * | 5/2020 |
| SU | 1007711 A1 | | 3/1983 |

OTHER PUBLICATIONS

Deka, et al. ; Quantum Dots: Low-Dosage Hydrate Inhibitors for Deep Water Flow Assurance ; Offshore Technology Conference, Houston, Texas ; May 2020.

(Continued)

*Primary Examiner* — Charles R Nold
(74) *Attorney, Agent, or Firm* — Oblon, McClelland, Maier & Neustadt, L.L.P.

(57) ABSTRACT

A method of inhibiting carbon dioxide ($CO_2$) hydrate formation in a $CO_2$ pipeline is described. The method includes injecting a composition including monoethylene glycol carbon quantum dots (MEG CQDs) into the $CO_2$ pipeline to deposit the MEG CQDs on an inside surface of the $CO_2$ pipeline. The method further includes pressurizing the $CO_2$ pipeline with a gas stream containing $CO_2$ and water vapor at a pressure of 200-2,000 pounds per square inch (psi). The MEG CQDs are present on the inside surface of the $CO_2$ pipeline in an amount effective to reduce the formation of $CO_2$ hydrates in the $CO_2$ pipeline during the pressurizing in comparison to the formation of the $CO_2$ hydrates in the $CO_2$ pipeline under the same conditions but in the absence of the MEG CQDs.

16 Claims, 15 Drawing Sheets

(51) Int. Cl.
  *C07C 29/76* (2006.01)
  *B82Y 30/00* (2011.01)
  *B82Y 40/00* (2011.01)
  *B82Y 20/00* (2011.01)
  *E21B 41/00* (2006.01)

(52) U.S. Cl.
  CPC .............. *B82Y 20/00* (2013.01); *B82Y 30/00* (2013.01); *B82Y 40/00* (2013.01); *C09K 2211/10* (2013.01)

(56) References Cited

U.S. PATENT DOCUMENTS

| | | | |
|---|---|---|---|
| 11,021,383 B2* | 6/2021 | Dhawan | C11D 7/3263 |
| 2008/0058229 A1* | 3/2008 | Berkland | C09K 8/60 |
| | | | 507/211 |
| 2013/0175046 A1* | 7/2013 | Morrison | C10L 3/107 |
| | | | 175/57 |

OTHER PUBLICATIONS

Bharathi, et al. Experimental and modeling studies on enhancing the thermodynamic hydrate inhibition performance of monoethylene glycol via synergistic green material ; Scientific Reports ; 2021.

* cited by examiner

METHOD OF INHIBITING CARBON DIOXIDE HYDRATE FORMATION

STATEMENT OF PRIOR DISCLOSURE BY THE INVENTOR

Aspects of the present disclosure are described in T. Saikia, J. Al-Jaberi, A. Sultan; "Synthesis and Testing of Monoethylene Glycol Carbon Quantum Dots for Inhibition of Hydrates in $CO_2$ Sequestration"; Jun. 1, 2021; ACS Omega; 6(23): 15136, incorporated herein by reference in its entirety.

BACKGROUND

Technical Field

The present disclosure is directed to a method of inhibiting carbon dioxide ($CO_2$) hydrate formation and particularly to a method of inhibiting carbon dioxide ($CO_2$) hydrate formation in a $CO_2$ pipeline.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Carbon capture for decarbonization and storage (CCS) is a method for addressing the problem of greenhouse gases in the atmosphere and reducing anthropogenic carbon dioxide ($CO_2$) emissions. A network of pipelines is used to transport the $CO_2$ from a source, such as a power plant, to a sink, such as a underground geological formation. $CO_2$ hydrate formation in the pipelines is a significant problem during transportation and injection phases. Clathrates, or $CO_2$ hydrates, are water-based crystalline solids in which non-polar molecules ($CO_2$) are trapped inside 'cages' of hydrogen-bonded, frozen water molecules. Several hydrate inhibitors, such as ethylene glycol, ethanol, methanol, and glycerol, are used to prevent the growth of the $CO_2$ hydrates. However, conventional hydrate inhibitors may require high concentrations, and solvent regeneration requiring high energy demand, exhibit toxicity, and/or may also need early replacements. Hence, there is a need for efficient methods which may substantially reduce or eliminate the above limitations.

SUMMARY

In an exemplary embodiment, a method of inhibiting a $CO_2$ hydrate formation in a $CO_2$ pipeline is described. The method includes injecting a composition including monoethylene glycol carbon quantum dots (MEG CQDs) into the $CO_2$ pipeline to deposit the MEG CQDs on an inside surface of the $CO_2$ pipeline. The method further includes pressurizing the $CO_2$ pipeline with a gas stream containing $CO_2$ and water vapor at a pressure of 200-2,000 pounds per square inch (psi). The MEG CQDs are present on the inside surface of the $CO_2$ pipeline in an amount effective to reduce the formation of $CO_2$ hydrates in the $CO_2$ pipeline during pressurizing in comparison to the formation of the $CO_2$ hydrates in the $CO_2$ pipeline under the same conditions but in the absence of the MEG CQDs.

In some embodiments, the MEG CQDs have an average size of 1-10 nanometers (nm), a substantially spherical shape, and a substantially crystalline structure.

In some embodiments, the MEG CQDs have a fluorescence emission at 320-420 nm after excitation with light at 280-370 nm.

In an exemplary embodiment, a method of making the MEG CQDs is disclosed. The method includes heating monoethylene glycol (MEG) to a temperature of 150-200 degrees Celsius (° C.) for 20-30 hours to form a reaction solution. The method further includes centrifuging and filtering the reaction solution to separate the MEG CQDs.

In some embodiments, the method includes pressurizing the $CO_2$ pipeline with a gas stream containing the $CO_2$ and water vapor at a pressure of 300-1,000 psi.

In some embodiments, the method includes pressurizing the $CO_2$ pipeline with a gas stream containing the $CO_2$ and water vapor at a pressure of 400-600 psi.

In some embodiments, the temperature of the inside surface of the $CO_2$ pipeline on which the MEG CQDs are deposited is 0-20° C. when pressurizing the $CO_2$ pipeline.

In some embodiments, inhibition of the $CO_2$ hydrate formation is maintained above 4° C. when pressurizing the $CO_2$ pipeline.

In some embodiments, inhibition of the $CO_2$ hydrate formation is maintained while pressurizing the $CO_2$ pipeline for at least 4,000 minutes.

In some embodiments, the MEG CQDs prevent agglomeration of the $CO_2$ hydrates in the $CO_2$ pipeline.

In some embodiments, the gas stream contains 3-7 volume percentage of (v.%) water based on the total volume of the gas stream.

In some embodiments, the amount effective of the MEG CQDs to reduce the formation of the $CO_2$ hydrates is 10-15 v.% of the volume of water in the gas stream.

In some embodiments, the gas stream contains 80-95 v.% $CO_2$, 3-7 v.% water, 0.1-2 v.% nitrogen gas, 0-1 v.% of at least one hydrocarbon, 0-1 v.% sulfur dioxide, and 0-1 v.% of at least one nitrogen oxide (NOX) gas, based on the total volume of the gas stream. The hydrocarbon is selected from a group including methane, ethane, propane, n-butane, iso-butane, n-pentane, and iso-pentane.

In some embodiments, the $CO_2$ pipeline connects a $CO_2$ emission source and a geological formation. The gas stream is injected into the geological formation for $CO_2$ sequestration.

In some embodiments, the geological formation is a depleted oil reservoir, a depleted gas reservoir, a saline formation, or an un-minable coal bed.

In some embodiments, the $CO_2$ pipeline connects a $CO_2$ source and an oil and/or gas reservoir. The gas stream is injected into the oil and/or gas reservoir for enhanced oil and/or gas recovery.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
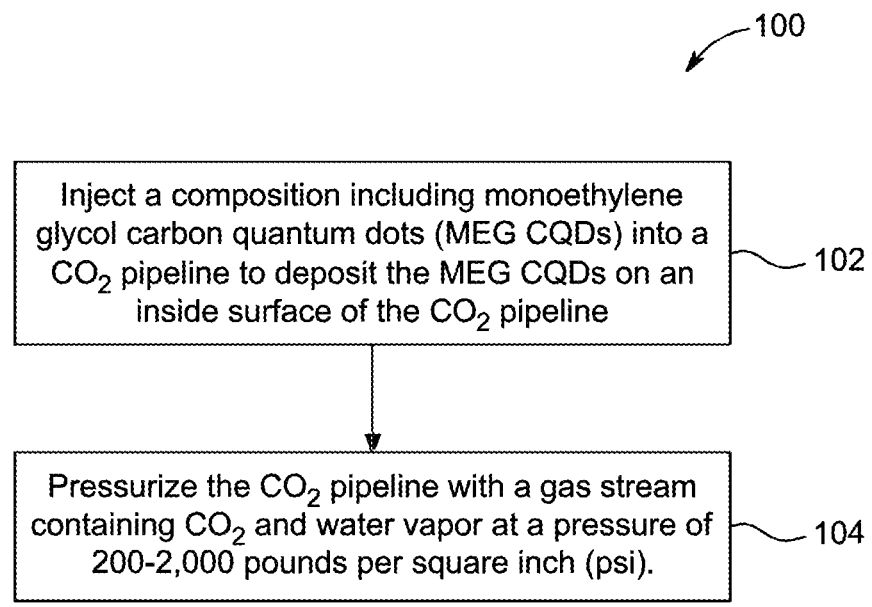
FIG. 1 is a flow chart of a method of inhibiting a $CO_2$ hydrate formation in a $CO_2$ pipeline, according to certain embodiments of the present disclosure.

In the drawings, like reference numerals designate identical or corresponding parts throughout the several views.

Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

Aspects of the present invention are directed towards inhibiting $CO_2$ hydrate formation in a $CO_2$ pipeline. The method involves capturing and storing $CO_2$ and further treating the captured $CO_2$ with hydrothermally synthesized monoethylene glycol carbon quantum dots (MEG CQDs), also referred to as CQDs, of the present disclosure. The prepared MEG CQDs were characterized using various analytical techniques, and the impact of the MEG CQDs on $CO_2$ hydrates was studied. The $CO_2$ hydrate inhibition properties of the MEG CQDs were compared to MEG. Although the description herein refers to inhibition of the $CO_2$ hydrate, it may be understood by a person skilled in the art that aspects of the present disclosure may be directed towards inhibition of other gases, as well. The method of the present disclosure inhibits the $CO_2$ hydrate formation by delaying a nucleation stage and preventing the $CO_2$ hydrate crystal growth process at lower concentrations than that of other commercial hydrate inhibitors. The $CO_2$ may be interchangeably referred to as the "gas".

Formation of the $CO_2$ hydrate, also referred to as the 'hydrate' or the 'gas hydrate', is the combination of the hydrate crystal nucleation process and the hydrate crystal growth process. The $CO_2$ consumption varies in the nucleation stage and the hydrate crystal growth stage of the hydrate formation. A first stage in the hydrate formation includes the dissolution of the $CO_2$ in water to form a solution. The second stage includes the nucleation of hydrate crystals. The third stage includes the hydrate crystal growth process. The hydrate crystal nucleation process is a microscopic phenomenon where tens of thousands of molecules participate. Hydrate nuclei are formed at the second stage, the nuclei are small labile clusters made up of water and gas molecules. The hydrate nuclei further grow and disperse in water. The hydrate nuclei gather gas in clusters until critical nuclei required for the hydrate crystal formation are obtained. The hydrate crystal grows and starts agglomerating. Mass transfer of the $CO_2$, growth kinetics, the hydrate crystal exothermic growth process, heat transfer from the hydrate crystal surface to the solution are associated with the hydrate crystal growth.

Figure 5:
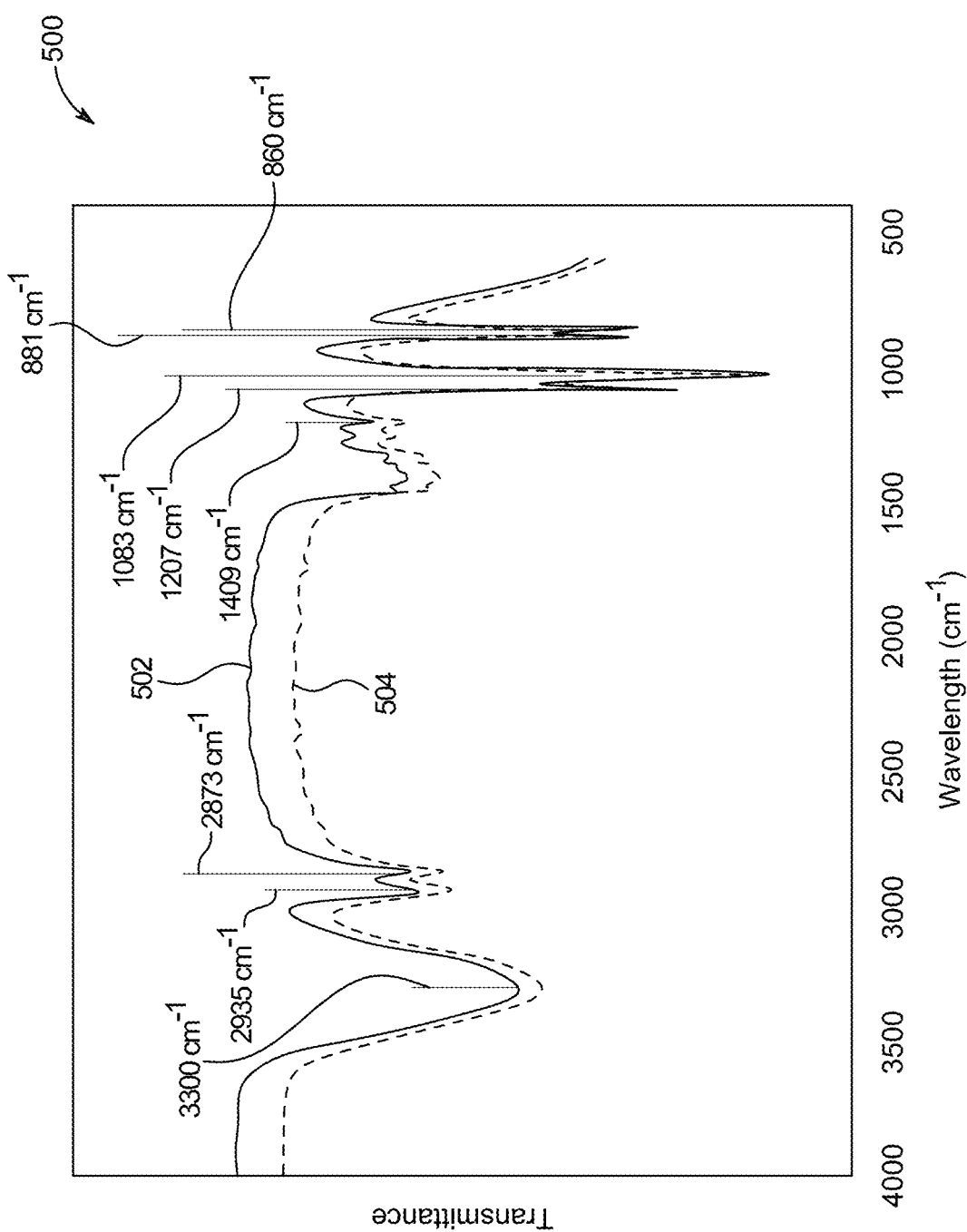
FIG. 5 is a graph representing comparative Fourier Transform Infrared Spectroscopy (FT-IR) spectra of MEG and MEG CQDs, according to certain embodiments.

In some embodiments, the MEG CQDs are made by heating MEG to a temperature of 150-200° C., preferably 160-190° C., or 170-180° C. for 20-30 hours, preferably 22-28 hours, or 24-26 hours, to form a reaction solution. In some embodiments, the MEG CQDs are made by heating MEG to a temperature of 180° C. for 24 hours to form the reaction solution. The method further includes centrifuging and filtering the reaction solution to separate the MEG CQDs. In some embodiments, the MEG CQDs have an average size of 1-10 nm, preferably 2-8 nm, or 4-5 nm, a substantially spherical shape, and a substantially crystalline structure. In some embodiments, the average interlayer distance of CQDs corresponds to crystalline graphite spacing (002) of 0.33-0.36 nm, preferably 0.34-0.35 nm. In an embodiment, the FTIR spectra of MEG and MEG CQDs are shown in FIG. 5. Both MEG and the MEG CQDs exhibit a similar peak structure indicating the presence of the same functional groups. Peaks at 3100-3600 cm$^{-1}$, preferably 3200-3400, or 3250-3350 cm$^{-1}$ are attributed to the vibration of the —OH group in the structure. Both peaks at 2920-

Figure 6:
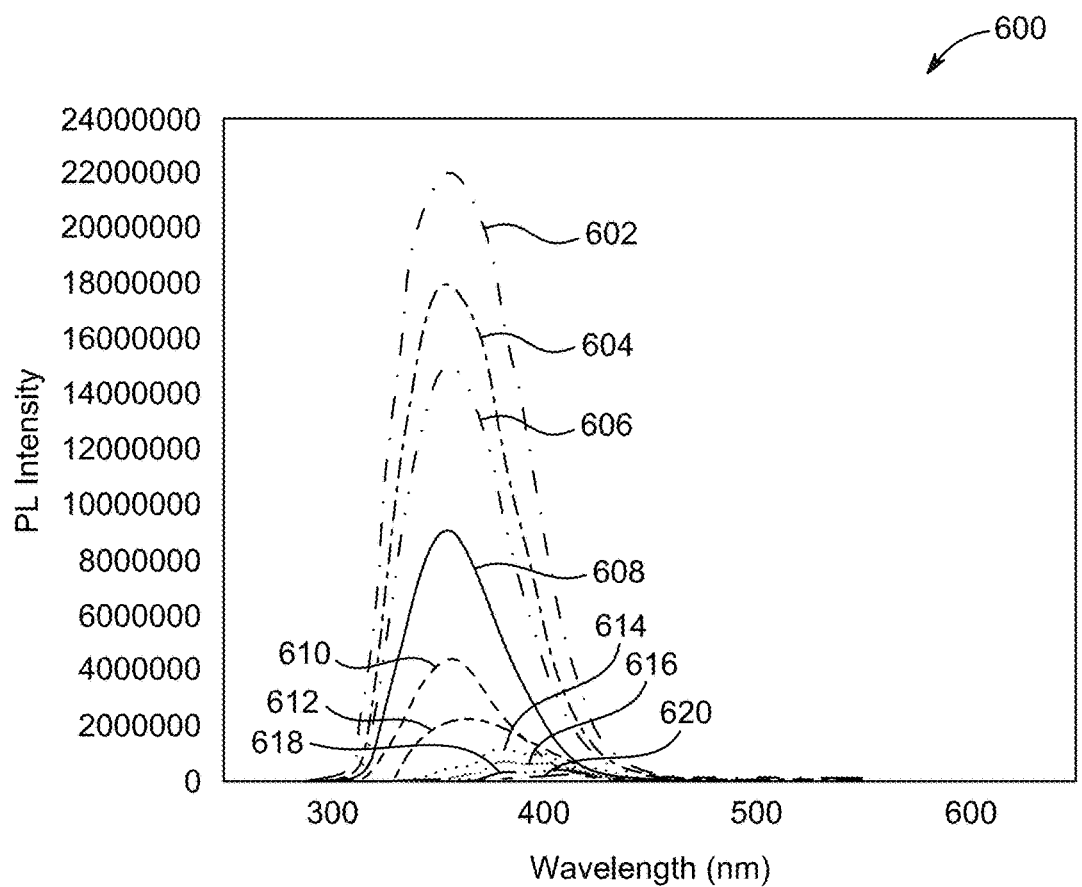
FIG. 6 is a graph representing excitation wavelength-dependent photoluminescence (PL) spectra of the MEG CQDs, according to certain embodiments.

2940, preferably 2925-2935 $cm^{-1}$ and 2860-2880 $cm^{-1}$, preferably 2865-2875 $cm^{-1}$ are attributed to the stretching between the C—H fragment carbon compounds. The stretching of C—C is reflected with the peak at 1200-1250 $cm^{-1}$, preferably 1210-1230 $cm^{-1}$. In some embodiments, the MEG CQDs have a fluorescence emission at 320-420 nm, preferably 340-400 nm, or 350-360 nm after excitation with light 280-370 nm, preferably 290-350 nm, or 305-315 nm. The PL spectrum of the synthesized CQDs is shown in FIG. 6.

Referring to FIG. 1, a flow chart of a method 100 of inhibiting the $CO_2$ hydrate formation in a $CO_2$ pipeline is illustrated. The order in which the method 100 is described is not intended to be construed as a limitation, and any number of the described method steps can be combined in any order to implement the method 100. Additionally, individual steps may be removed or skipped from the method 100 without departing from the spirit and scope of the present disclosure.

At step 102, the method 100 includes injecting a composition including the MEG CQDs into the $CO_2$ pipeline to deposit the MEG CQDs on an inside surface of the $CO_2$ pipeline. At step 104, the method 100 further includes pressurizing the $CO_2$ pipeline with a gas stream containing the $CO_2$ and water vapor at a pressure of 200-2,000 psi. In some embodiments, the pressure while pressurizing the $CO_2$ pipeline with the gas stream is 300-1000 psi. In some embodiments, the pressure while pressurizing the $CO_2$ pipeline with the gas stream is 400-600 psi. The MEG CQDs are present on the inside surface of the $CO_2$ pipeline in an amount effective to reduce the formation of the $CO_2$ hydrates in the $CO_2$ pipeline while pressurizing the $CO_2$ pipeline with the gas stream in comparison to the formation of the $CO_2$ hydrates in the $CO_2$ pipeline under the same conditions but in the absence of the MEG CQDs. In some embodiments, if hydrates are formed, the MEG CQDs prevent agglomeration of the $CO_2$ hydrates in the $CO_2$ pipeline.

The MEG CQDs are preferably injected into the $CO_2$ pipeline at a location that is downstream of the upstream-most end of the $CO_2$ pipeline. This arrangement accommodates a $CO_2$ feed port that is unobstructed by the CQD injection facilities. The $CO_2$ pipeline may terminate at an upstream end at one or more $CO_2$ sources. Typically the $CO_2$ pipeline is connected to a plurality of $CO_2$ sources which sequentially join the $CO_2$ pipeline at locations that are upstream of the CQD injection point. In this manner the CQDs are injected downstream of all points at which $CO_2$ is injected or fed into the $CO_2$ pipeline. Other additives and/or adjuvants may be injected downstream from the $CO_2$ CQD injection point such as anti-corrosives, lubricants or sealants. However, preferably no additional $CO_2$-containing gas or liquid is injected into the $CO_2$ pipeline downstream of the point from which CQDs are injected.

Preferably a single $CO_2$ pipeline has multiple CQD injection points, each preferably located downstream from all $CO_2$ injection points. For example, the $CO_2$ pipeline may have CQD injection points regularly spaced along its length downstream from the downstream-most $CO_2$ addition point. CQD injection points are preferably regularly spaced along the circumference of the inner surface of the $CO_2$ pipeline such that a single CQD injection facility has a ring-like tube with injection points for a CQD-containing composition regularly spaced around the inner circumference of the $CO_2$ pipeline. Similar facilities may be located regularly lengthwise along the $CO_2$ pipeline, for example, each 10 m, 50 m, 100 m, 200 m, 300 m, 500 m or each kilometer along the length of the $CO_2$ pipeline.

The injection point at which a CQD-containing composition is injected into the $CO_2$ pipeline is preferably in the form of a nozzle which dispenses liquid compositions in a fine mist or spray such as a spray nozzle equipped with ultrasonic transducer and a low profile face. Preferably, the nozzle extends no further into the $CO_2$ pipeline than 0.1 mm, 0.25 mm, 0.5 mm or 1 mm. Preferably the CQD-dispensing nozzle has a face that is coplanar with the inside surface of the $CO_2$ pipeline.

In some embodiments, the temperature of the inside surface of the $CO_2$ pipeline on which the MEG CQDs are deposited is 0-20° C., preferably 4-15° C., or 8-10° C. when pressurizing the $CO_2$ pipeline with the gas stream. In some embodiments, inhibition of the $CO_2$ hydrate formation is maintained above 4° C., preferably 4-40° C., or 4-20° C. when pressurizing the $CO_2$ pipeline with the gas stream. In some embodiments, inhibition of the $CO_2$ hydrate formation is maintained while pressurizing the $CO_2$ pipeline with the gas stream for at least 4,000 minutes, preferably 4,000-10,000 minutes, or throughout the entire pressurization.

In some embodiments, the gas stream contains 3-7 volume % (v %) water, preferably 3-5 v % or 3-4 v % based on the total volume of the gas stream. In some embodiments, the effective amount of the MEG CQDs to reduce the formation of the $CO_2$ hydrates is 10-15 v %, preferably 10-13 v %, or 10-11 v %, of the volume of the water. In an embodiment, the gas stream contains 80-95 v % $CO_2$, preferably 85-95 v %, or 90-95 v %, 3-7 v % water, preferably 3-5 v %, or 3-4 v %, 0.1-2 v.% nitrogen gas, preferably 0.5-1.5 v %, or 1-1.2 v %, 0-1 v % of one or more hydrocarbons, preferably 0-0.5 v %, or 0-0.1 v %. 0-1 v % sulfur dioxide, preferably 0-0.5 v %, or 0-0.1 v % and 0-1 v % of one or more nitrogen oxide (NOX) gases preferably 0-0.5 v %, or 0-0.1 v %., based on the total volume of the gas stream. In some embodiments, the hydrocarbon is selected from a group including methane, ethane, propane, n-butane, iso-butane, n-pentane, and iso-pentane. In an embodiment, the gas stream contains 95 v % $CO_2$, 3 v % water, 1 v % nitrogen gas, and 1 v % sulfur dioxide.

In some embodiments the $CO_2$ pipeline connects a $CO_2$ emission source and a geological formation. In some embodiments, the $CO_2$ emission source may include, but is not limited to, facilities burning oil, coal, and/or gas. In some embodiments, the geological formation is a depleted oil reservoir, a depleted gas reservoir, a saline formation, or an un-minable coal bed. In some embodiments, the $CO_2$ pipeline connects a $CO_2$ source and an oil and/or gas reservoir. In an embodiment, the gas stream is injected into the geological formation for $CO_2$ sequestration. In an alternate embodiment, the gas stream is injected into the oil and/or gas reservoir for enhanced oil and/or gas recovery.

EXAMPLES

The following examples describe and demonstrate exemplary embodiments of the method 100 described herein. The examples are provided solely for the purpose of illustration and are not to be construed as limitations of the present disclosure, as many variations thereof are possible without departing from the spirit and scope of the present disclosure.

Materials Required Monoethylene glycol, $CO_2$ gas was provided with a purity of 99.9%.

Example 1: Method of Preparation

A hydrothermal method was used for the synthesis of the MEG CQDs. An undiluted MEG sample was subjected to a high temperature of 180° C. for 24 h in a hydrothermal cell to form a reaction solution. The hydrothermal cell was made up of Teflon™-encapsulated stainless steel. The MEG sample was placed inside the hydrothermal cell and sealed using a spring-loaded cap to maintain the high pressure inside the hydrothermal cell developed during heating. The reaction solution was further centrifuged and filtered to obtain the MEG CQDs. The MEG CQDs obtained were stored in a refrigerator below 4° C.

Example 2: Characterization

The optical properties of the MEG CQDs were tested using 365 nm UV light, UV-VIS absorption spectroscopy (USB-2000, OceanOptics, USA), and PL spectroscopy (HoribaFluorolog 3 fluorescence spectrometer). Size and structure analyses of the MEG CQDs were performed using HRTEM (JOEL JEM 2100F). The TENSOR 27 (BRUKER) FT-IR spectrometer was used to study an infrared spectrum of absorption or emission of the MEG CQDs. The MEG and MEG CQDs FTIR spectra were compared to compare chemical functional groups. Raman spectra of the MEG and MEG CQDs were acquired with a LabRAM HR Evolution Raman spectrometer. The spectrometer was furnished with a Helium-Neon (HeNe) laser (<20 milliwatts (mW)). The Raman spectra were obtained at an excitation wavelength of 633 nm.

Example 3: Experiment: Gas Hydrate Inhibition Study

Figure 2:
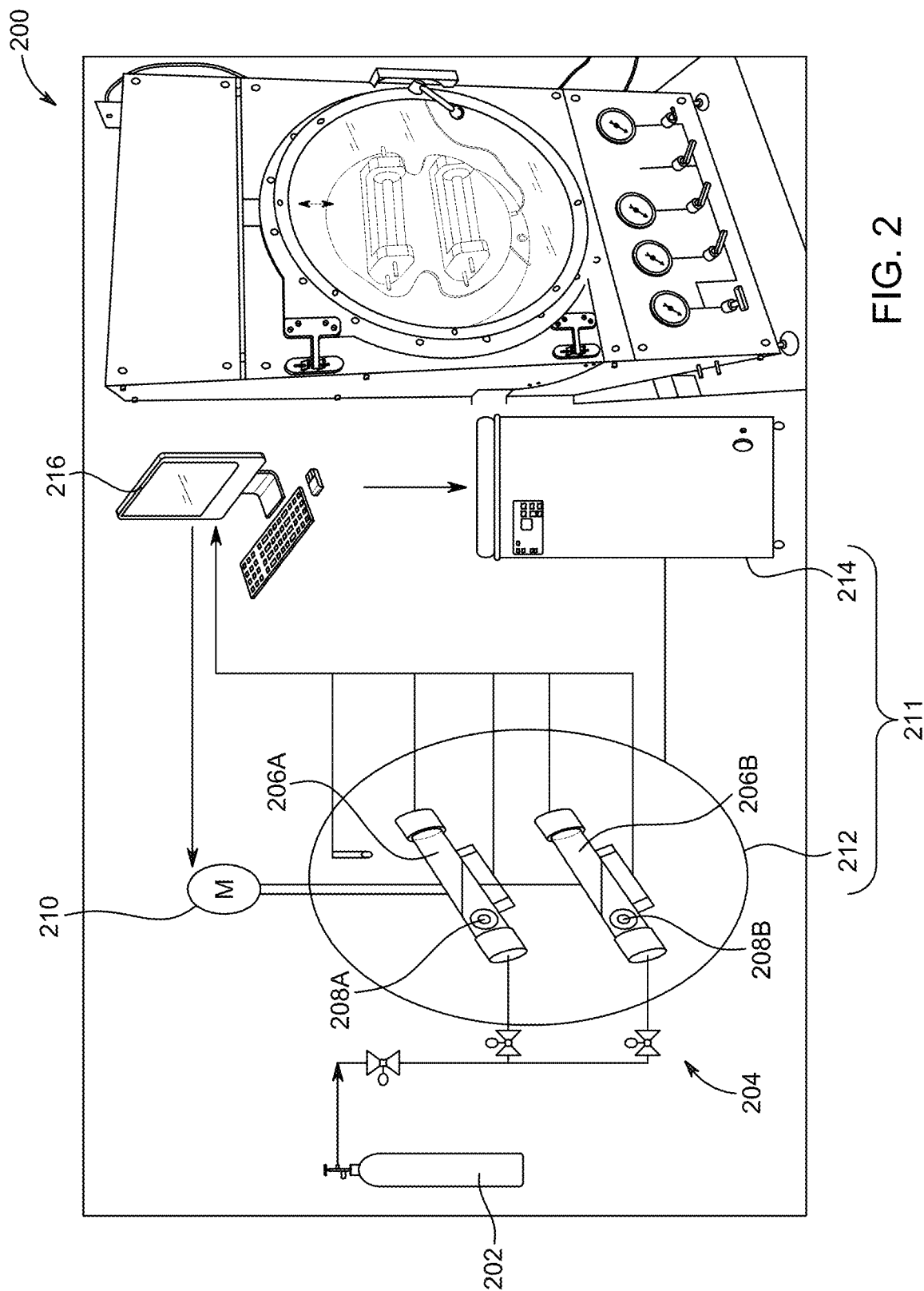
FIG. 2 is a perspective view of a PSL Systemtechnik™ high-pressure sapphire rocking cell system; according to certain embodiments of the present disclosure.

Referring to FIG. 2, a perspective view of a PSL System-technik™ high-pressure sapphire rocking cell system 200, otherwise referred to as the 'system 200', is illustrated. System 200 includes a source 202 and a plurality of flowlines 204 to fluidly couple the source 202 to a first sapphire cell 206A and a second sapphire cell 206B of the system 200. The system 200 may include more than two sapphire cells in some embodiments. The first sapphire cell 206A and the second sapphire cell 206B are collectively referred to as the 'sapphire cells 206' or are individually referred to as the 'sapphire cell 206', unless otherwise specified. The sapphire cells 206 include the first and second ends. Sensors are installed at the first and second ends of the sapphire cells 206. In an embodiment, the sapphire cells 206 have diameter of 12.7 millimeters (mm). In an embodiment, the sapphire cells 206 include volume of 20 milliliters (mL). In some embodiments, the volume and diameter of the sapphire cells 206 may vary depending on the customized needs of the system 200. The system 200 is further connected to a motor 210 to rock the sapphire cells 206.

The first and second sapphire cells 206A 206B further include a first ball 208A and a second ball 208B, respectively. The first ball 208A and the second ball 208B are collectively referred to as the 'balls 208' or individually referred to as the 'ball 208' unless otherwise specified. In an embodiment, the balls 208 are made up of stainless steel. In some embodiments, the balls 208 may be made up of a material such as iron, aluminum, copper, bronze, brass. In the present embodiment, the balls 208 have a diameter of 10.16 mm. The balls 208 provide agitation in experimental solutions during the working of the system 200. Further, time taken by the ball 208 to travel from the first end of the sensor to the second end of the sensor in the sapphire cell 206 refers to ball run time. The ball run time provides information about agglomeration characteristics of hydrate crystals, pumpability of a dispersed hydrate crystal solution, and intrinsic viscosity changes in a multiphase hydrate crystal slurry. A longer ball running time indicates the increase in viscosity of the hydrate crystal slurry in sapphire cells. The rapid formation and growth of the hydrate crystals in the solution lead to increased viscosity of the hydrate crystal slurry. Finally, the agglomeration of the hydrate crystals increases the ball run time to higher values.

The system 200 also includes an automated temperature control unit 211, including a water bath 212 and a chiller 214. The automated temperature control unit 211 controls the temperature of the sapphire cells 206. The system 200 further includes a computer system 216 for data acquisition and programming.

An experiment was started by charging the sapphire cells 206 with the experimental solutions including 10 mL of distilled water and thermodynamic hydrate inhibitors (THI) solutions (i.e., MEG or MEG CQDs were added to distilled water with 10.0% volume by volume (v/v) percentage) and placing the sapphire cells 206 inside the water bath 212. The water bath 212 was filled with water, and the sapphire cells 206 were flushed four times using the $CO_2$ to purge air molecules from the sapphire cells 206 and the plurality of flowlines 204. The pressure was raised in the sapphire cells 206 using the $CO_2$ to the desired pressure (i.e., ~450-500 psi), and the temperature was lowered to 5.0° C. A rocking frequency was set to 15 times/minute. The pressure ranging between 430 and 480 psi was maintained in the sapphire cells 206 at 5.0° C. The sapphire cells 206 temperature decreased from 5.0 to 2.0° C. with a prolonged cooling rate of 0.1° C./h and then from 2.0 to 1.0° C. at a cooling rate of 0.5° C./hour (h). The temperature was stabilized for 4 h. A point where a sudden pressure drop occurs indicates the point of a gas hydrate induction. In an embodiment, data was matched with captured images of the sapphire cells 206 as the gas hydrate inhibitor slows down the hydrate formation and leads to inconspicuous pressure drop. The condition of the experimental solutions in the sapphire cells 206 was photographically captured and saved every 1.0 minute in the computer system 216. The experiment was further repeated.

Example 4: Volumetric Gas Uptake Calculation

The number of moles of the gas entrapped in a solid hydrate phase at any point of the experiment can be calculated with the help of an equation (1).

$$\Delta n_t = \left(\frac{PV}{ZRT}\right)_{t=0} - \left(\frac{PV}{RT}\right)_t \qquad (1)$$

Here, P is the sapphire cell pressure, V is the gaseous volume, T is the sapphire cell temperature, R is the ideal gas constant, Z is the compressibility factor (the gas compressibility factor was estimated using Pitzer correlations).

In the experimental solution, the $CO_2$ gas dissolution takes place before hydrate nucleation and the major portion of the dissolved $CO_2$ participated in the hydrate crystal formation as a guest molecule. In the gas hydrate crystal, the $CO_2$ is captured and separated from the gas phase. The equation (1) is valid for calculating the number of moles of the gas entrapped in the gas hydrate crystals during the experiment with variation in the sapphire cells 206 temperature, as the sapphire cells 206 form a closed system, and, during the investigation, the temperature variations lead to consequent pressure variations. Hence, temperature and pressure are considered in equation (1). The $CO_2$ hydrate crystals form a cubic hydrate structure (SI) where each unit cell includes 46 water molecules and up to 8 $CO_2$ molecules. The $CO_2$ molecules occupy the hydrate crystal's pentagonal dodecahedral and tetra decahedral cavities. One-unit cell includes six large cages and two small cages. When all cages of the hydrate crystals are occupied, a hydration number is 5.75. However, based on CSMGem calculations under equilibrium conditions, a hydration number of 7.03 is considered. The water conversion to hydrates (%) can be calculated with the help of the hydration number by an equation (2).

$$\% \, n_w^t = \frac{7.03 \times \Delta n_t}{n_w^0} \times 100 \quad (2)$$

Here, $n_w^0$ is the number of moles of water (initial) in the sapphire cell 206. To compare the experiments with different pressure and temperature conditions, the normalized gas uptake value was calculated by using an equation (3).

$$g_t = \frac{\Delta n_t}{n_w^0} \text{(mole of gas per mole of water)} \quad (3)$$

Volumetric gas uptake that compares the experiments with different experimental conditions can be calculated using an equation (4).

$$vg_t = \frac{\Delta n_t \times 22400}{\left(n_w^0 - 7.03 \Delta n_t\right)\left(\frac{MW_{H_2O}}{\rho_{H_2O}}\right) + \left(\Delta n_t \times \frac{MW_{hydrate}}{\rho_{hydrate}}\right)} \quad (4)$$

Here, $MW_{H2O}$ is the molecular weight of water, $\rho_{H2O}$ is the density of water, $MW_{hydrate}$ is the molecular weight of the hydrate, and $\rho_{hydrate}$ is the density of the hydrate. The volumetric gas uptake was calculated after the induction point of the hydrate in the experimental solution to study the effect of the hydrate inhibitor and the volumetric gas uptake represents the hydrate growth. The dissolution of the $CO_2$ in the liquid phase before the hydrate crystal induction point was not considered.

MEG CQDs Characterization

Figure 3B:
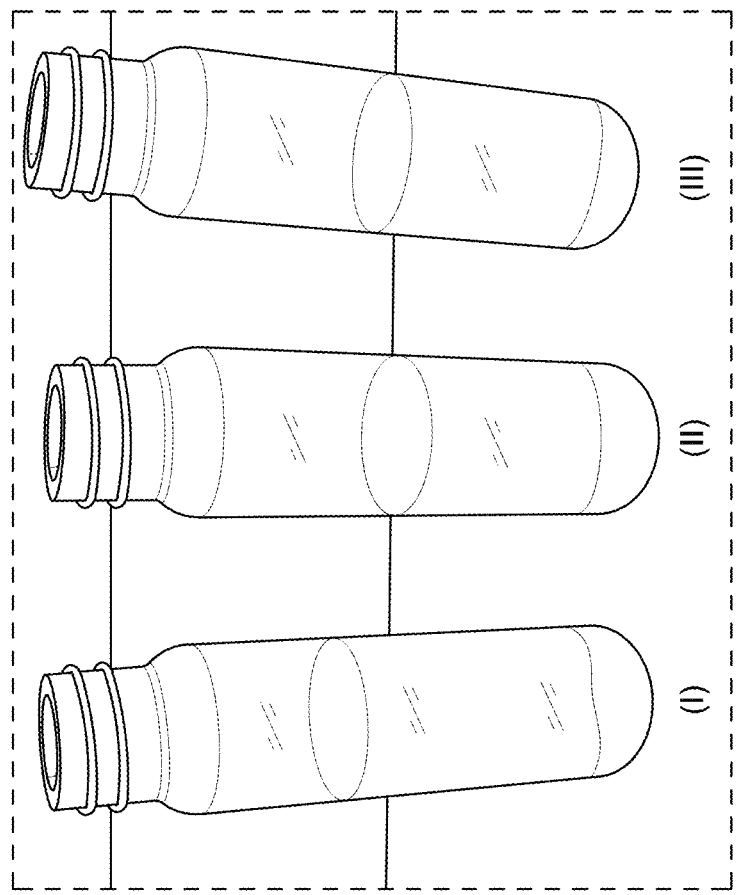
FIG. 3B is an image representing the effect of samples placed under UV light, according to certain embodiments.
Figure 3A:
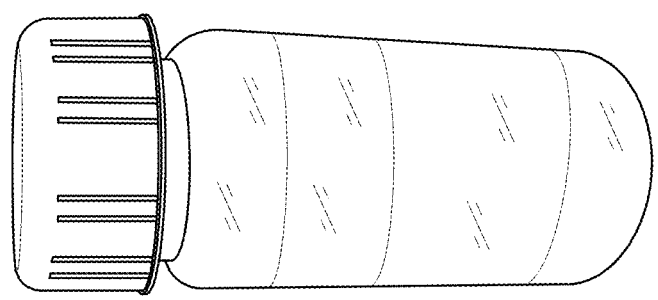
FIG. 3A is an image representing the effect of MEG CQDs placed under visible light, according to certain embodiments.

Referring to FIGS. 3A-3B, images representing the effect of samples placed under visible and UV light (365 nm), respectively, are illustrated. FIG. 3A shows a vial containing the MEG CQDs placed under visible light. FIG. 3B shows a first vial including the MEG, a second vial including the MEG CQDs and a third vial 3 including distilled water (which acts as a control), placed under UV light. The MEG CQDs under visible light showed no colour and were transparent (FIG. 3A). The first vial including the MEG and the third vial including distilled water (FIG. 3B) also showed no fluorescence under UV light. However, the second vial showed strong bluish colour fluorescence emission under UV light. The fluorescence emission shown by the MEG CQDs may be attributed to a 'quantum confinement' effect. Blueshift of the MEG CQDs was observed under UV light.

Figure 4B:
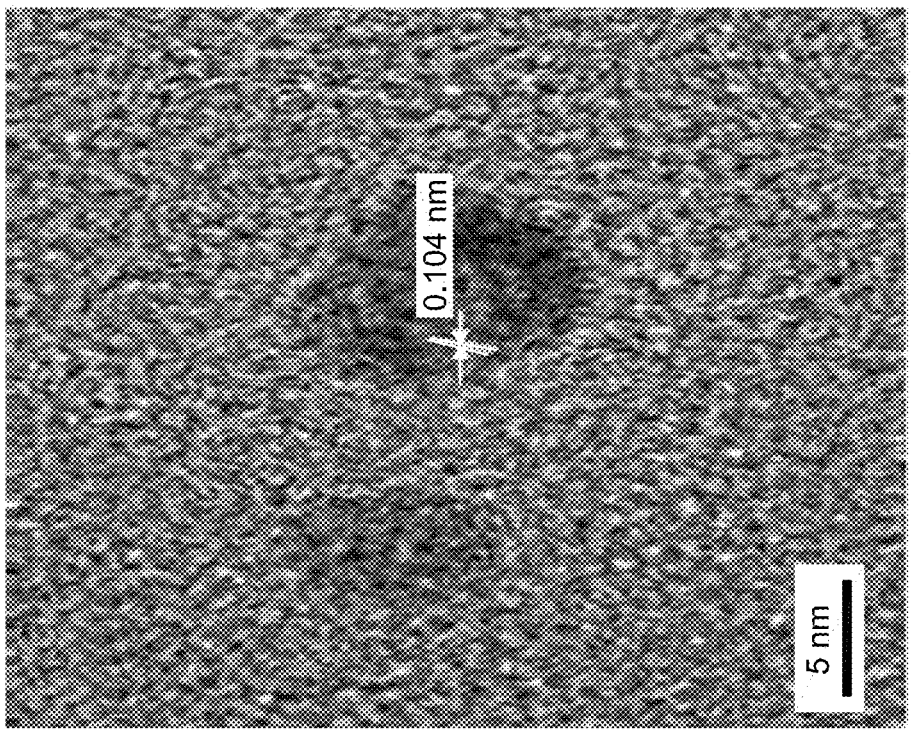
FIG. 4B is the HR-TEM image of the MEG CQDs at 5 nm, according to another embodiment.
Figure 4A:
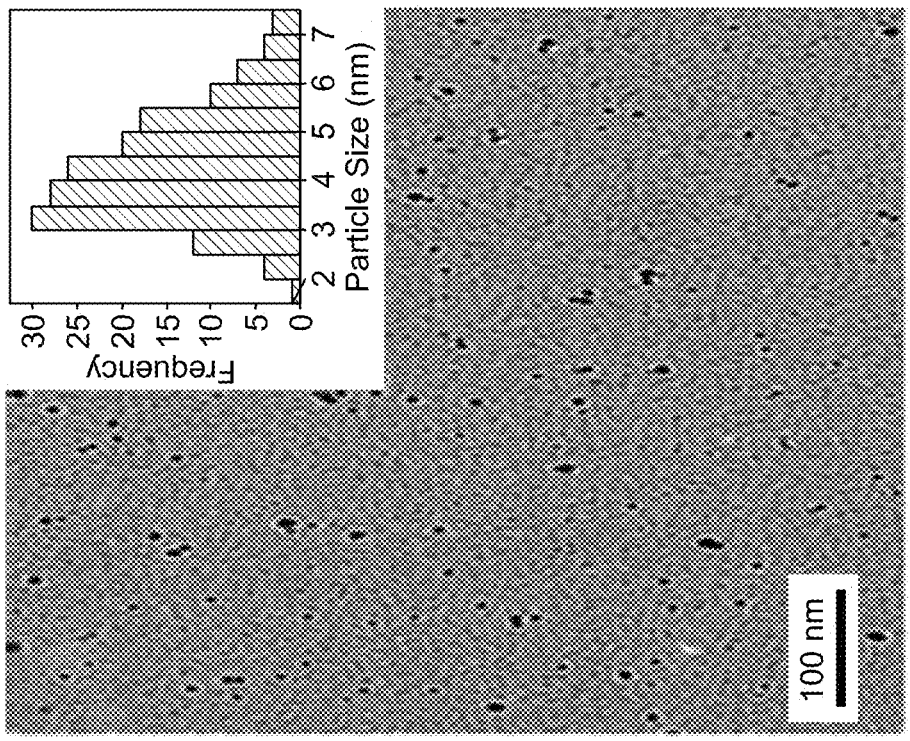
FIG. 4A is a high-resolution transmission electron microscopy (HR-TEM) image of the MEG CQDs at 100 nm, according to another embodiment.

Referring to FIGS. 4A-4B, HR-TEM images of the MEG CQDs at 100 and 5 nm, respectively, are illustrated. FIGS. 4A-4B show spherical shape and uniform size of the MEG CQDs. FIGS. 4A-4B also show monodispersed MEG CQDs. From FIG. 4B, lattice fringes within the MEG CQDs, indicating crystalline characteristics can be observed. The lattice spacing in the MEG CQDs was found to be 0.104 nm. Conventionally synthesized CQDs from a synthetic molecular carbon source or natural source show an entire amorphous structure or amorphous outer shell with a crystalline core. However, the hydrothermally synthesized CQDs of the present disclosure have a complete crystalline structure with narrower particle size distribution of the MEG CQDs. The average particle size distribution of the MEG CQDs was 4.3 nm (FIGS. 4A-4B).

Referring to FIG. 5, a graph 500 representing comparative FT-IR spectra of the MEG and MEG CQDs is illustrated. The graph 500 includes a first trend line 502 representing the MEG and a second trend line 504 representing the MEG CQDs. Peaks at 3300 $cm^{-1}$; 2935 and 2873 $cm^{-1}$; 1207 $cm^{-1}$ can be attributed to vibrations of a —OH group; stretching between a C—H bond; and stretching of a C—C bond, respectively. No change was seen in the absorption peaks of the first and second trend lines 502, 504. Hence, FIG. 5 confirms that the MEG CQDs include similar functional groups as the MEG.

Figure 7:
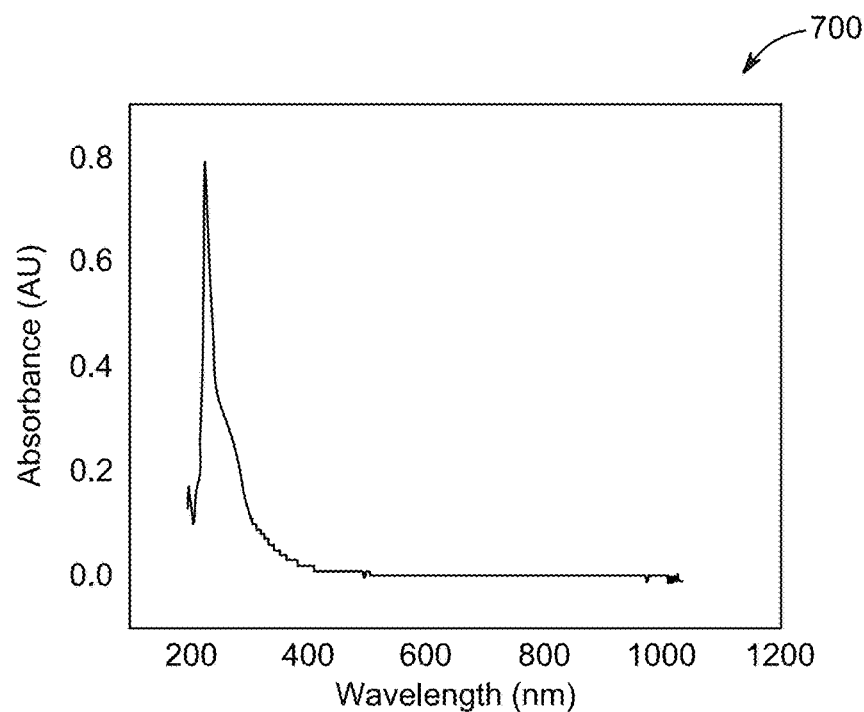
FIG. 7 is an ultraviolet-visible (UV-Vis) spectrum of the MEG CQDs, according to certain embodiments.

Referring to FIG. 6, a graph 600 representing excitation wavelength-dependent PL spectra of the MEG CQDs is illustrated. Emission intensity changed with increasing an excitation wavelength. The graph 600 shows a first trend line 602 referring to 280 nm, a second trend line 604 referring to 290 nm, a third trend line 606 referring to 300 nm, a fourth trend line 608 referring to 310 nm, a fifth trend line 610 referring to 320 nm, a sixth trend line 612 referring to 330 nm, a seventh trend line 614 referring to 340 nm, an eighth trend line 616 referring to 350 nm, a ninth trend line 618 referring to 360 nm, and a tenth trend line 620 referring to 370 nm. The graph 600 shows changes in the intensity emission as the excitation wavelength changes from the first trend line 602 to the tenth trend line 610 (refer to 280 to 370 nm). The highest emission intensity was observed at the excitation wavelength of 310 nm and was cantered at 359 nm A UV-VIS spectrum 700 of the MEG CQDs is illustrated in FIG. 7. An absorption peak of the MEG CQDs at 228 nm represents the σ-σ* electronic transition of C—C on the MEG CQD surface.

Figure 8:
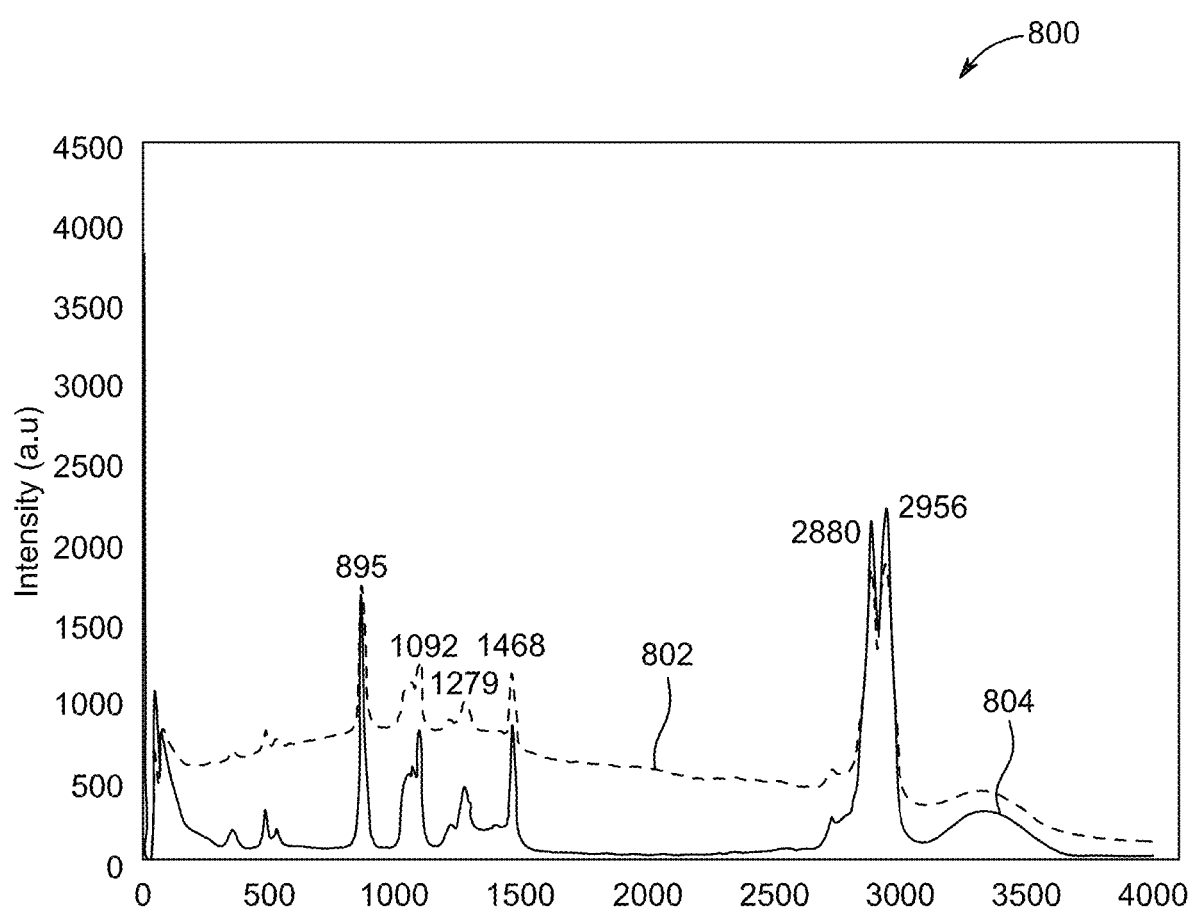
FIG. 8 is a graph representing comparative Raman spectra of MEG and MEG CQDs, according to certain embodiments.

Referring to FIG. 8, a graph 800 representing Raman spectra of the MEG and MEG CQDs is illustrated. The Raman spectroscopy was used to identify the aggregation of CQDs in the MEG. The graph 800 includes a first trend line 802 representing the MEG CQDs and a second trend line 804 representing the MEG. The first trend line, 802 shows fingerprints of CQDs in the MEG at 1092 $cm^{-1}$, 1468 $cm^{-1}$, and 1279 $cm^{-1}$. An increase in the intensity of 15% was observed compared to the second trend line 804. The increase in the intensity of the MEG CQDs may be attributed to the small size of the MEG CQDs. The small size of the MEG CQDs may lead to surface-enhanced Raman scattering with surface plasmon resonances. However, no Raman shift due to aggregation of CQDs was observed. The first trend line 802 and second trend line 804 provided a ratio of 0.98 for peaks at 2880 $cm^{-1}$ and 2956 $cm^{-1}$.

MEG and MEG CQD Hydrate Inhibition Testing

The hydrate inhibition efficiency of the MEG and the MEG CQDs (at 10% v/v concentration) in water under the $CO_2$ hydrate equilibrium conditions are shown in FIGS. 9-13. The initial temperature and pressure conditions in the sapphire cells 206 were maintained at 5° C. and ~450-500 psi in all the experiments, respectively. The MEG has two hydroxyl groups that restrict the water molecules from forming the hydrate crystal cages by making hydrogen bonds with multiple water molecules. An aqueous phase chemical potential of the hydrate formation decreases with increasing concentration of the MEG in the aqueous phase. Hence, the hydrate's decreased chemical potential results in shifting the hydrate equilibrium conditions toward the higher pressure and lower temperature region. The kinetics of the hydrate crystal nucleation and formation is dependent on the MEG concentration in the aqueous phase. The hydrate crystals start to grow when a system surpasses the free-energy barrier to the hydrate crystal nucleation. With the increase in the MEG concentration, the affinity of the MEG toward the water molecules increases, which retards the hydrate structure and phase relaxation and hinders the water molecule rearrangement to form hydrates. Increased concentration of the MEG resulted in a longer induction time and a slower growth rate of the hydrate crystals.

Figure 9:
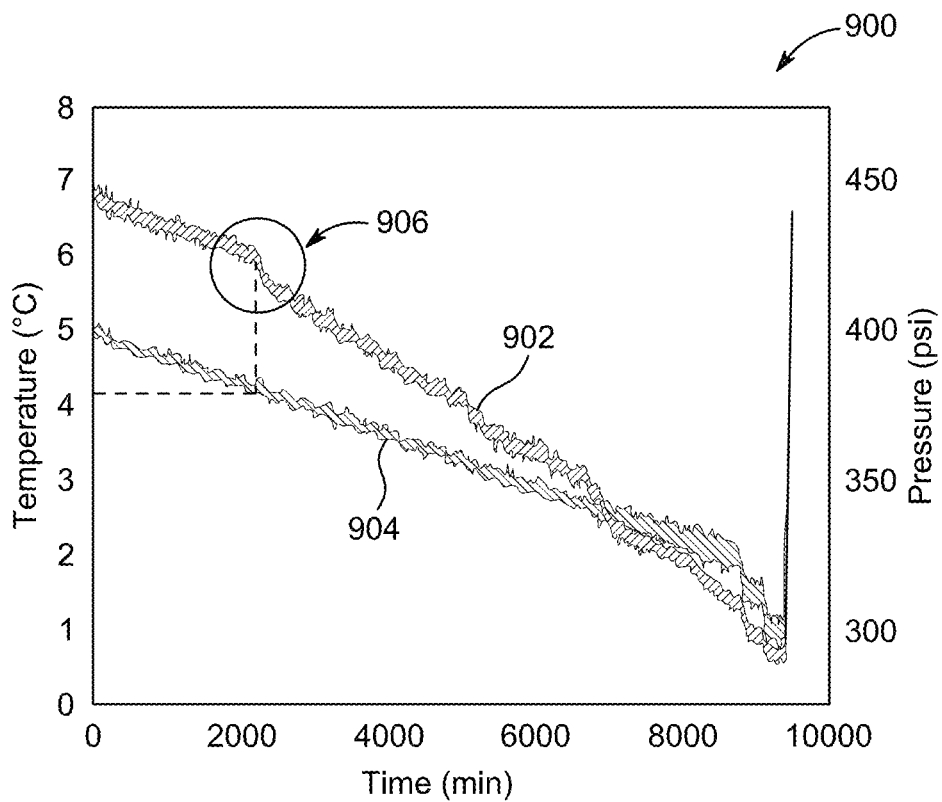
FIG. 9 is a graph representing a $CO_2$ hydrate inhibition using MEG (MEG inhibition 1 experiment), according to certain embodiments.

Referring to FIG. 9, a graph 900 representing the $CO_2$ hydrate inhibition using the MEG (MEG inhibition 1 experiment) is illustrated. The graph 900 includes a first trend line 902 referring to pressure and a second trend line 904 referring to temperature. The first trend line 902 shows a sudden pressure drop in the sapphire cells 206 which further leads to the induction of the hydrate crystals at 2247 minutes. The rate of the hydrate crystal formation and the hydrate crystal growth was rapid as indicated by the rapid pressure drop after the hydrate induction point. A circle 906 shows a sudden pressure in the first trend line 902. However, the second trend line 904 shows inhibition of the hydrate nucleation up to 4.18° C. by the MEG.

Figure 10:
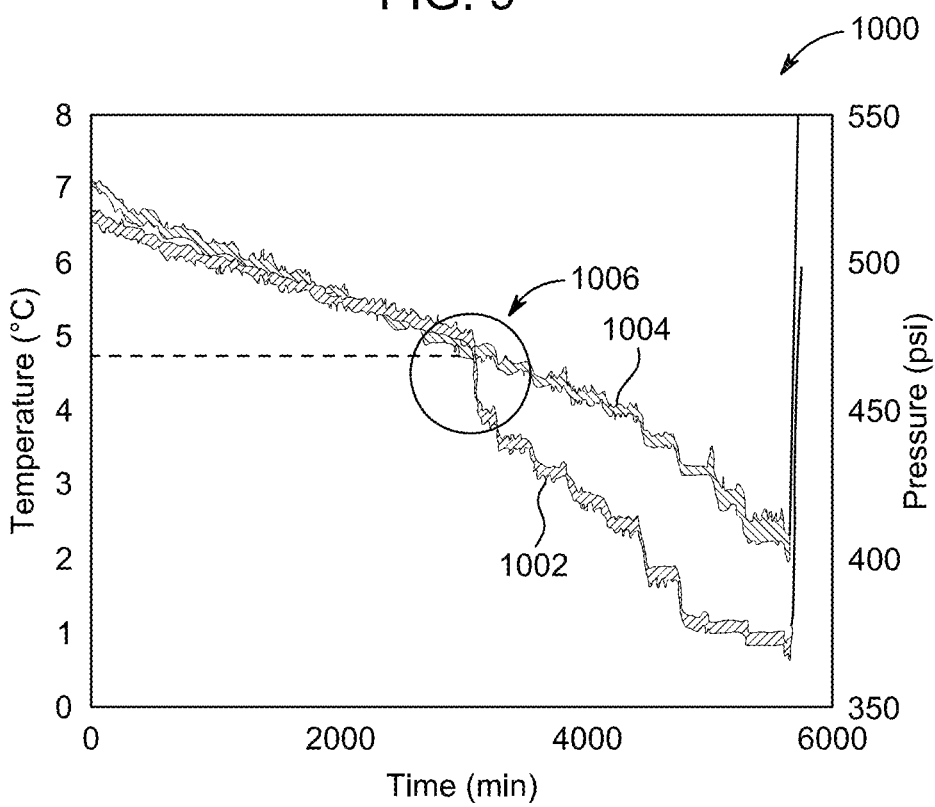
FIG. 10 is a graph representing the $CO_2$ hydrate inhibition using MEG (MEG inhibition 2 experiment), according to certain embodiments.
Figure 14A:
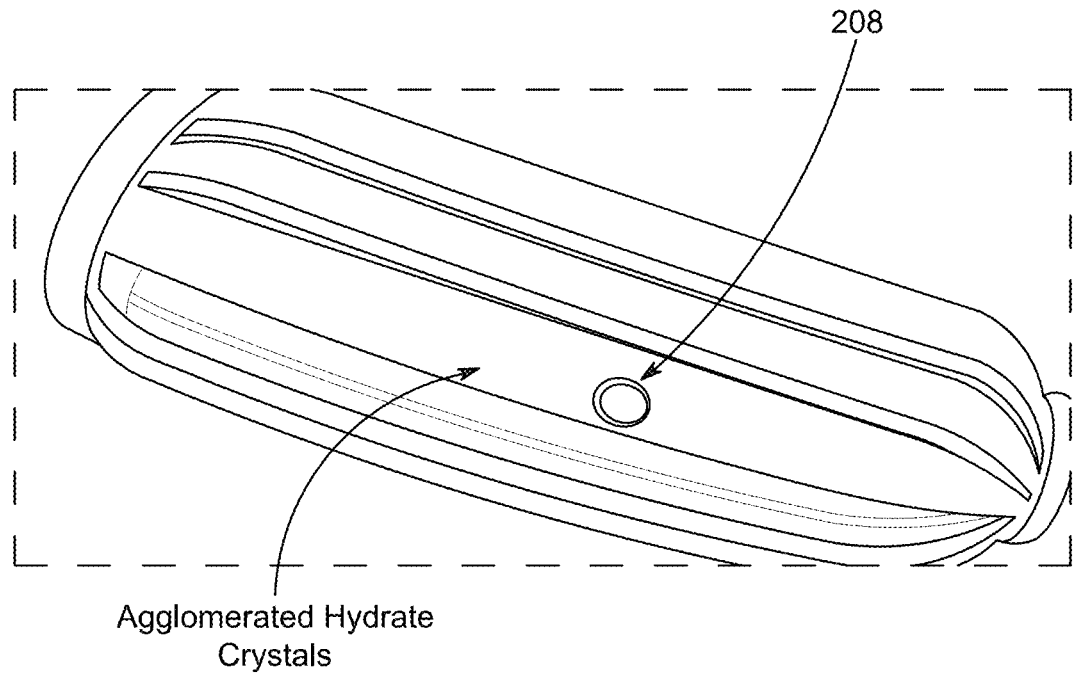
FIG. 14A is an image representing blockage of a sapphire cell with the $CO_2$ hydrate, according to certain embodiments.

Referring to FIG. 10, a graph 1000 representing the $CO_2$ hydrate inhibition using the MEG (MEG inhibition 2 experiment) is illustrated. The graph 1000 includes a first trend line, 1002 referring to pressure, and a second trend line, 1004 referring to temperature. The graph 1000 shows the formation of the $CO_2$ hydrate at 4.85° C. after 2900 minutes. A circle 1006 shows a sudden pressure drop and consequently a high crystal rate growth. As shown in FIG. 14A, the hydrate crystals started to grow and agglomerate, which blocked the sapphire cell 206 completely.

Figure 11:
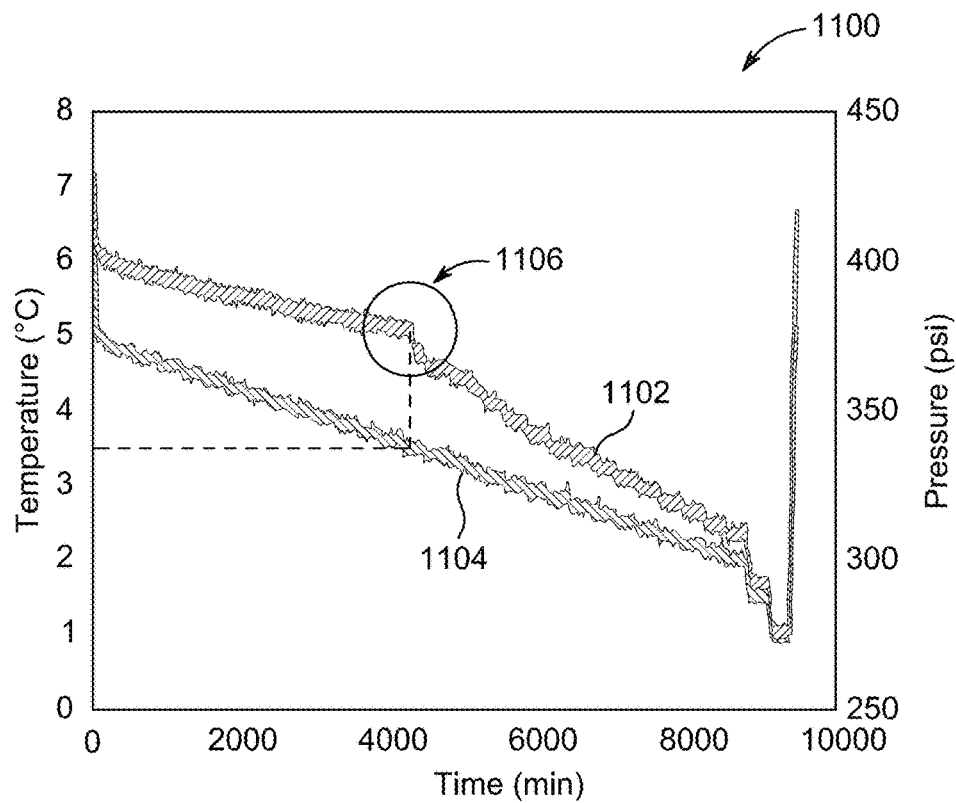
FIG. 11 is a graph representing the $CO_2$ hydrate inhibition using the MEG CQDs (MEG CQDs inhibition 1 experiment), according to certain embodiments.
Figure 14B:
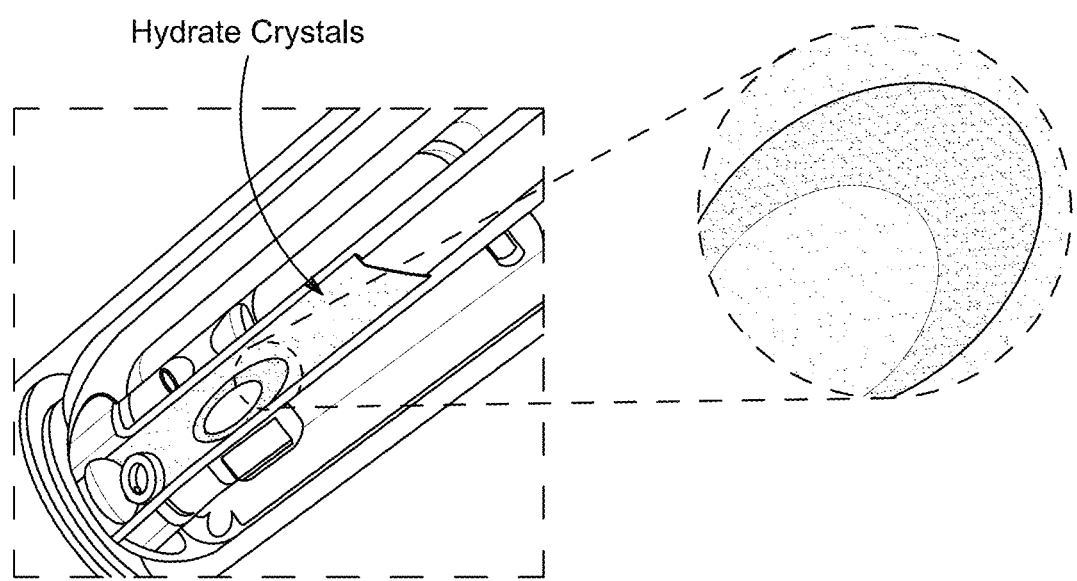
FIG. 14B is an image representing no blockage in the sapphire cell, according to certain embodiments.

Referring to FIG. 11, a graph 1100 representing the $CO_2$ hydrate inhibition using the MEG CQDs (MEG inhibition 1 experiment) is illustrated. The graph 1100 includes a first trend line 1102 referring to pressure and a second trend line 1104 referring to temperature. A circle 1106 shows a sudden pressure drop in the first trend line 1102. The first trend line, 1102 shows that the induction time was increased to 4123 minutes compared to 2247 or 2900 minutes induction time of the hydrate crystals in using the MEG in MEG inhibition 1 and 2 experiments. The pressure drop rate after the hydrate induction point is slow and gradual compared to the MEG inhibition experiments. Further, the second trend line, 1104 shows that the $CO_2$ hydrate crystal induction dropped to a temperature of 3.52° C. Moreover, the agglomeration of the hydrate crystals was prevented by the MEG CQDs, which was verified by the ball run time and visual inspection of the sapphire cell 206 pictures. The gas hydrate crystals in the sapphire cell 206 remain in a slurry form until the end of a cooling cycle, as shown in FIG. 14B.

Figure 12:
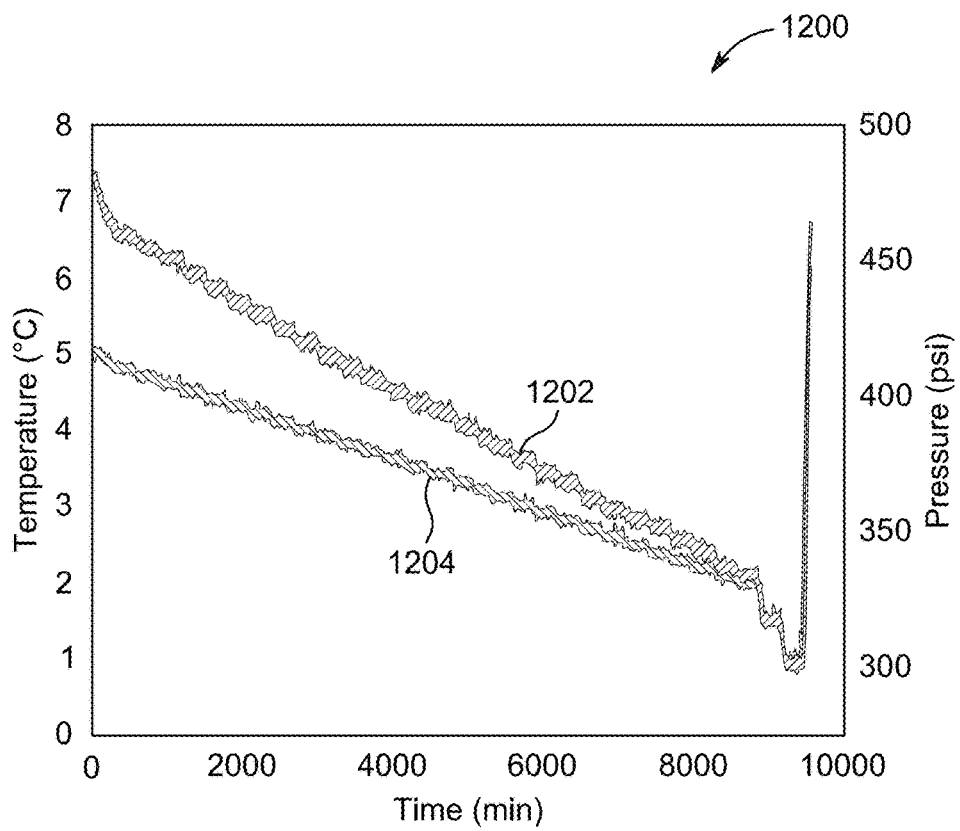
FIG. 12 is a graph representing the $CO_2$ hydrate inhibition using the MEG CQDs (MEG inhibition 2 experiment), according to certain embodiments.
Figure 13:
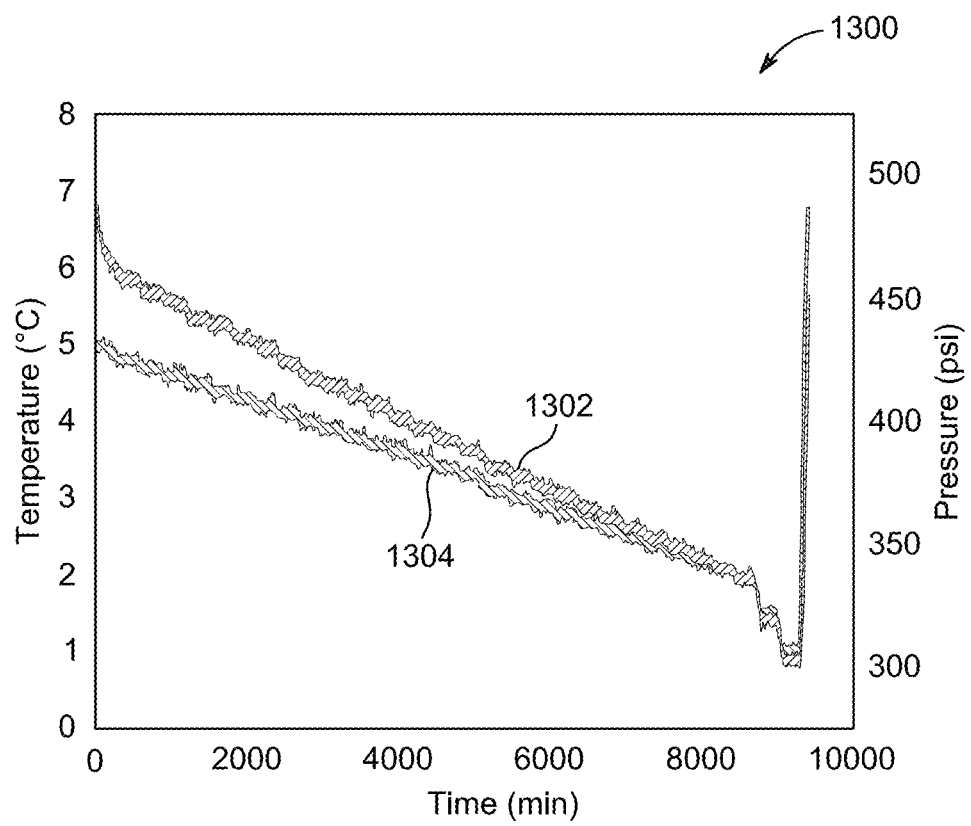
FIG. 13 is a graph representing the $CO_2$ hydrate inhibition using the MEG CQDs (MEG inhibition 3 experiment), according to certain embodiments.

FIG. 12 and FIG. 13 refer to experimental graphs 1200 and 1300 of repeated experiments (i.e., MEG CQD inhibition 2 and 3 experiments), respectively. The graph 1200 includes a first trend line 1202 referring to pressure and a second trend line 1204 referring to temperature Similarly, graph 1300 includes a first trend line 1302 referring to pressure and a second trend line 1304 referring to temperature. The absence of sudden pressure drop points is observed in FIGS. 12 and 13 co-relating to retardation in the $CO_2$ hydrate nucleation and growth by the MEG CQDs in the sapphire cells 206. The $CO_2$ hydrate crystals agglomeration was also not seen in the sapphire cell 206 until the end of the experiment.

The hydrate induction point was further identified in the experiments (MEG CQD inhibition 2 and 3) by taking partial reference to ball run time. The $CO_2$ hydrate crystal induction in the MEG CQD inhibition 2 experiment was found to be at ~3.3° C. with an induction time of ~5100 minutes. Similarly, in the MEG CQD inhibition 3 experiment, the $CO_2$ hydrate crystal induction was found at ~3.4° C. and an induction time of ~4800 minutes (Table1).

TABLE 1

$CO_2$ hydrate induction time and temperature

| Sl. no. | Experiment | $CO_2$ hydrate induction temperature (° C.) | $CO_2$ hydrate induction time (min) |
|---|---|---|---|
| 1 | MEG inhibition 1 | 4.18 | 2247 |
| 2 | MEG inhibition 2 | 4.85 | 2900 |
| 3 | MEG CQD inhibition 1 | 3.52 | 4123 |
| 4 | MEG CQD inhibition 2 | 3.3* | 5100* |
| 5 | MEG CQD inhibition 3 | 3.4* | 4800* |

*Time and temperature data noted visually and with partial reference to ball run time Table 1 provides mean values of the $CO_2$ hydrate induction temperature and induction time of the MEG inhibition experiments compared to the MEG CQD inhibition experiments. The mean hydrate induction temperature for the MEG inhibition experiment is ~4.5° C., and the hydrate induction time is ~2573 min. The mean values for the MEG CQD inhibition experiment are ~3.4° C. and ~4674 min.

Figure 15:
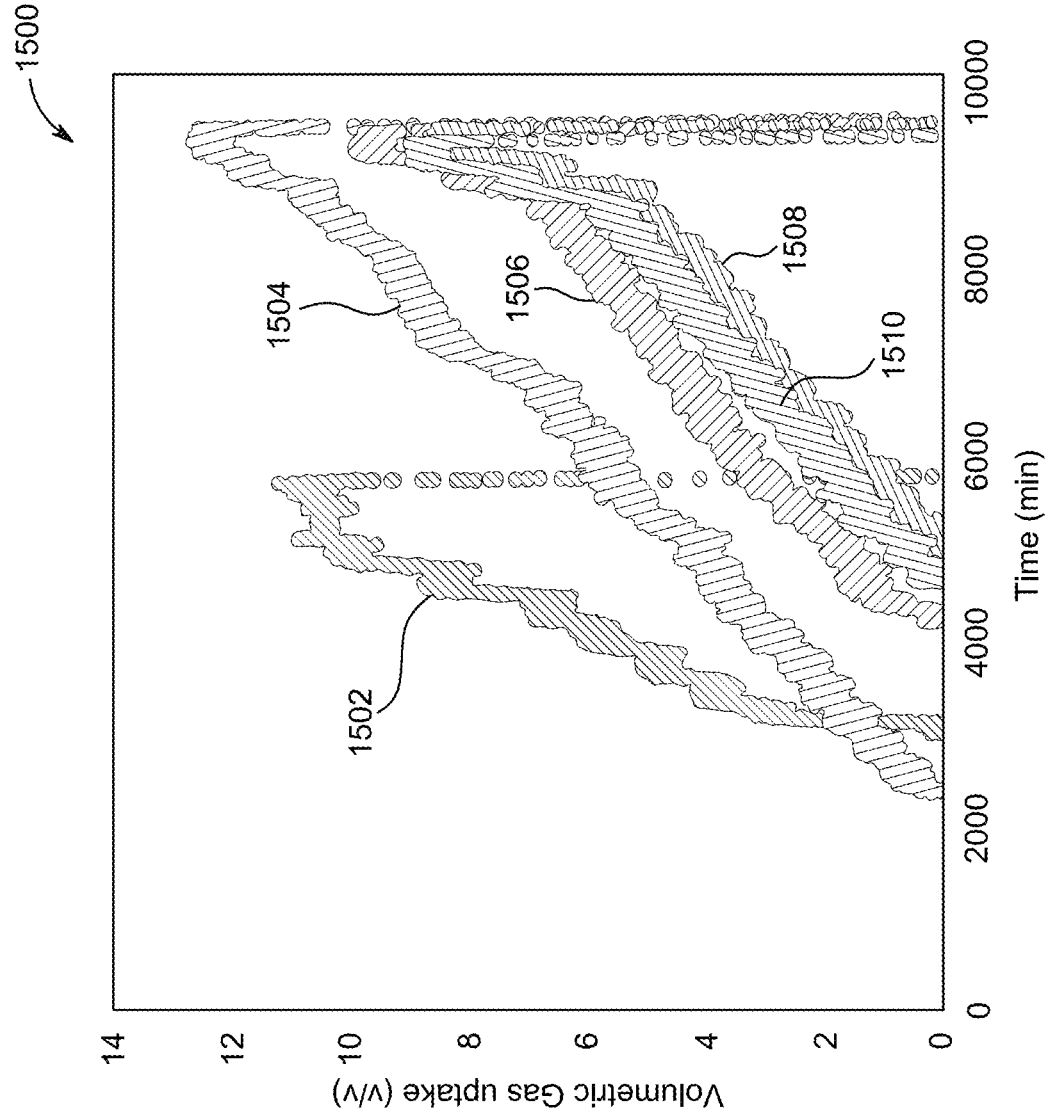
FIG. 15 is a graph representing comparative data of volumetric gas uptake in various experiments, according to certain embodiments.

Referring to FIG. 15, a graph 1500 representing comparative data of volumetric gas uptake in different experiments is illustrated. The graph 1500 includes a first trend line 1502 referring to the volumetric gas uptake in the MEG inhibition 1 experiment, a second trend line 1504 referring to the volumetric gas uptake in the MEG inhibition 2 experiment, a third trend line 1506 referring to the volumetric gas uptake in the MEG CQD inhibition 1 experiment, a fourth trend line 1508 referring to the volumetric gas uptake in the MEG CQD inhibition 2 experiment, and a fifth trend line 1510 referring to the volumetric gas uptake in the MEG CQD inhibition 3 experiment. The hydrate crystal induction point in the experiment was the point of origin of the $CO_2$ entrapment in the hydrate crystals. Graph 1500 and Table 2 provide total gas uptake values.

TABLE 2

Total volumetric gas uptake

| S. no. | Experiment | Total volumetric gas uptake (v/v) |
|---|---|---|
| 1 | MEG inhibition 1 | 11.21 |
| 2 | MEG inhibition 2 | 12.64 |
| 3 | MEG CQD inhibition 1 | 9.92 |
| 4 | MEG CQD inhibition 2 | 8.68 |
| 5 | MEG CQD inhibition 3 | 9.02 |

As per graph 1500 and table 2, it can be observed that the first trend line 1502 and the second trend line 1504 are steep with the total gas uptake value of about 11.21 v/v and 12.64 v/v, respectively. The third, fourth, and fifth trend lines 1506, 1508, 1510 are not as steep as the first and second trend lines 1502, 1504, and the total volumetric gas uptake values were reduced to 9.92, 8.68, and 9.02 v/v. Data in graph 1500 confirms more efficiency in restricting the hydrate crystal growth with the MEG CQDs when compared to the MEG.

Figure 16:
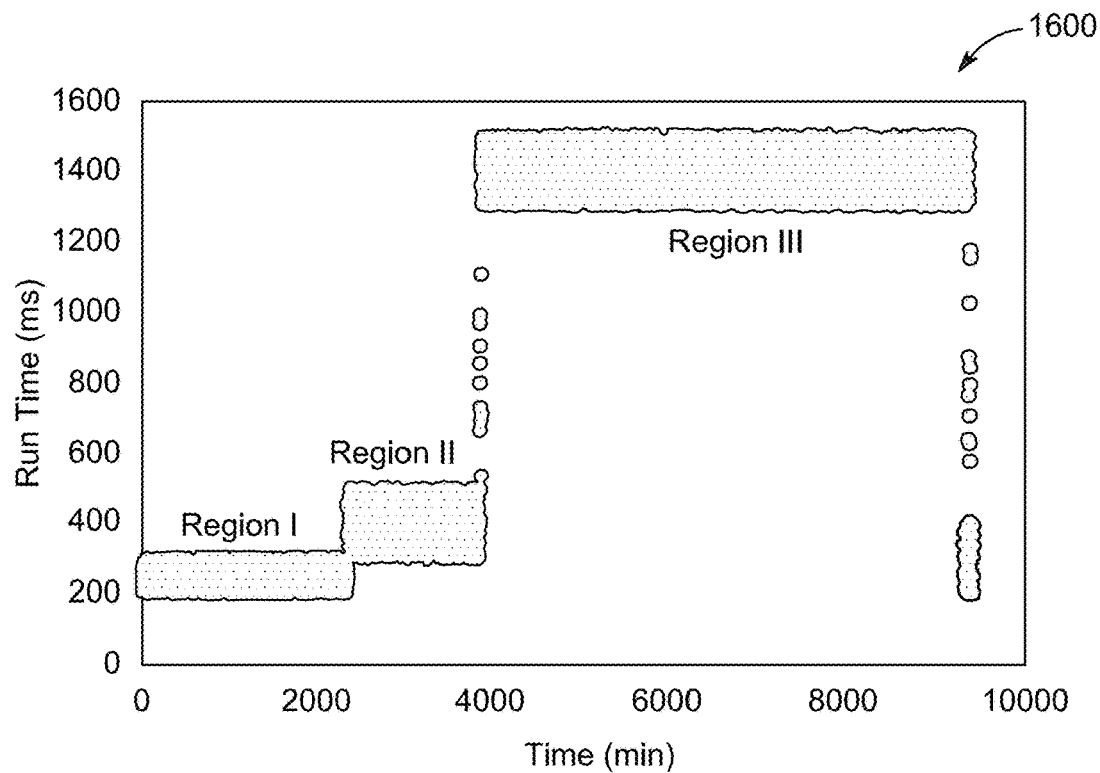
FIG. 16 is a ball run time plot for the MEG inhibition 1 experiment, according to certain embodiments.

To statistically compare the MEG and MEG CQD anti-agglomeration characteristics, the ball run times were compared. Referring to FIG. 16, a plot 1600 representing a change in ball run time during the MEG inhibition 1 experiment is illustrated. Plot 1600 may be interchangeably referred to as the ball run time plot 1600. The plot includes region I, region II, and region III. Region I represents the state of the experimental solution before the induction of hydrate crystals in the sapphire cell 206. The ball run time is between 200 and 300 minutes. The change in ball run time at around 2338 minutes indicated the induction of hydrate crystals in the experimental solution and was designated as region II. The ball run time was increased to 500 minutes and maintained between 300 and 500 minutes. After approximately 3828 minutes, another ball run time was observed; the ball run time was increased to 1500 minutes, indicating further growth of hydrate crystals in the experimental solution and partial agglomeration (confirmed visually). That region was designated as region III. Only a partial agglomeration of hydrate crystals was visible; a complete hydrate block was not seen until the end of the experiment.

Figure 17:
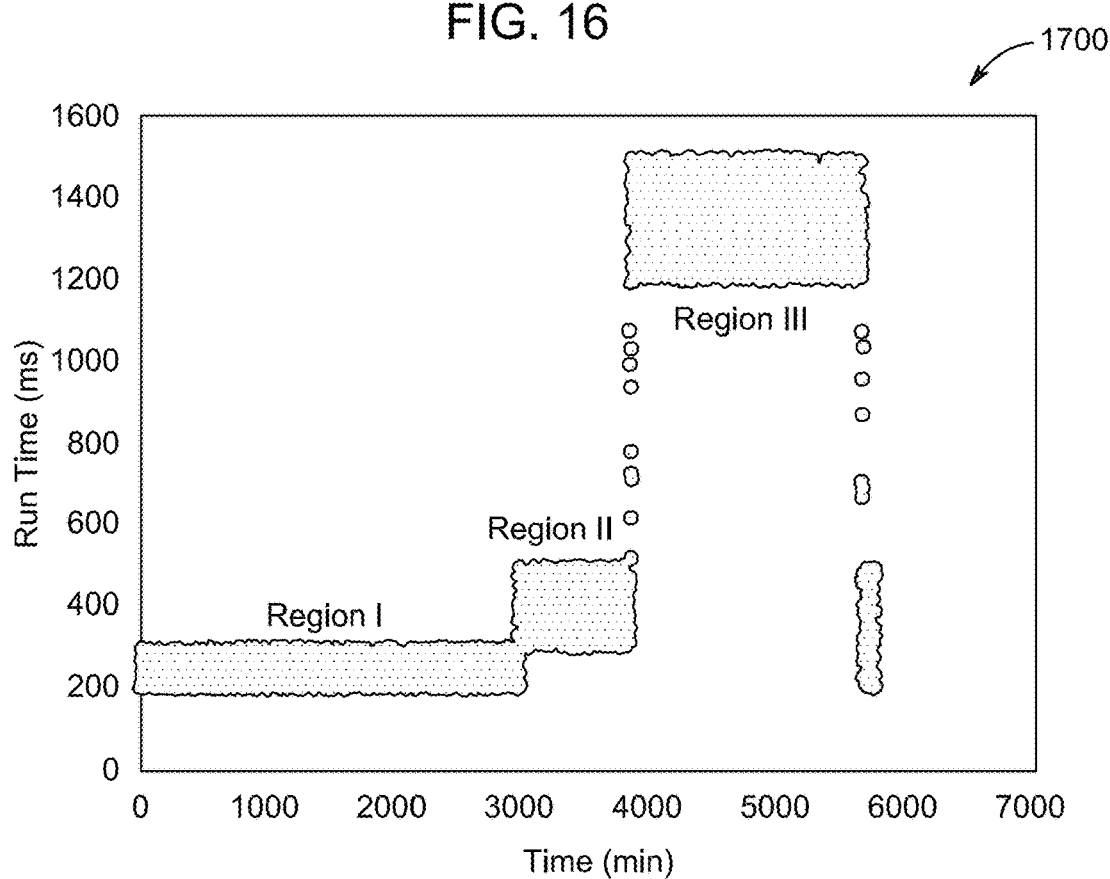
FIG. 17 is the ball run time plot for the MEG inhibition 2 experiment, according to certain embodiments.

Similar behavior was seen in the MEG inhibition 2 experiment; in the region I, the ball run time was maintained between 200 and 300 minutes (FIG. 17—plot 1700). Approximately 2968 minutes, the ball run time was increased to 500 minutes in region II. In region III, the ball run time was increased to 1500 minutes. In the MEG inhibition 2 experiment, the hydrate crystals agglomerated and formed a hydrate block at the middle portion of the sapphire cell 206 (as shown in FIG. 14A). The experiment was stopped after the formation of the hydrate block.

Figure 18:
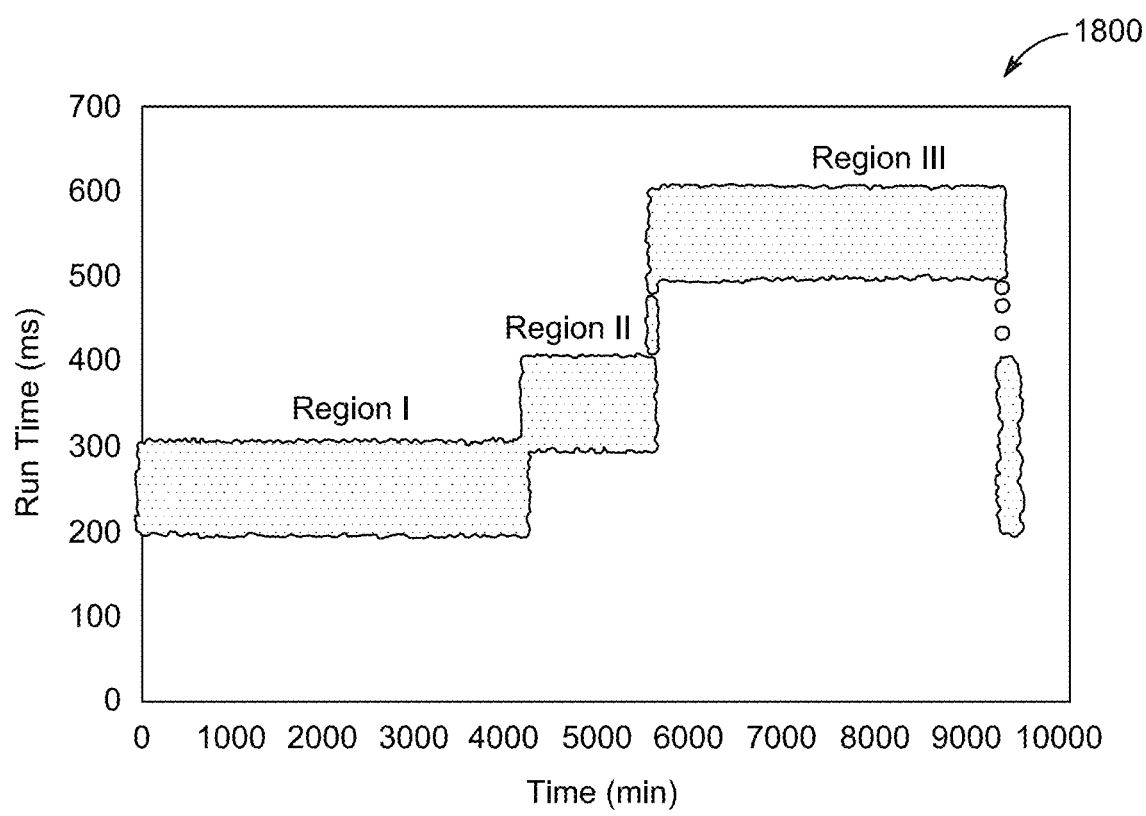
FIG. 18 is the ball run time plot for the MEG CDQs inhibition 1 experiment, according to certain embodiments.
Figure 19:
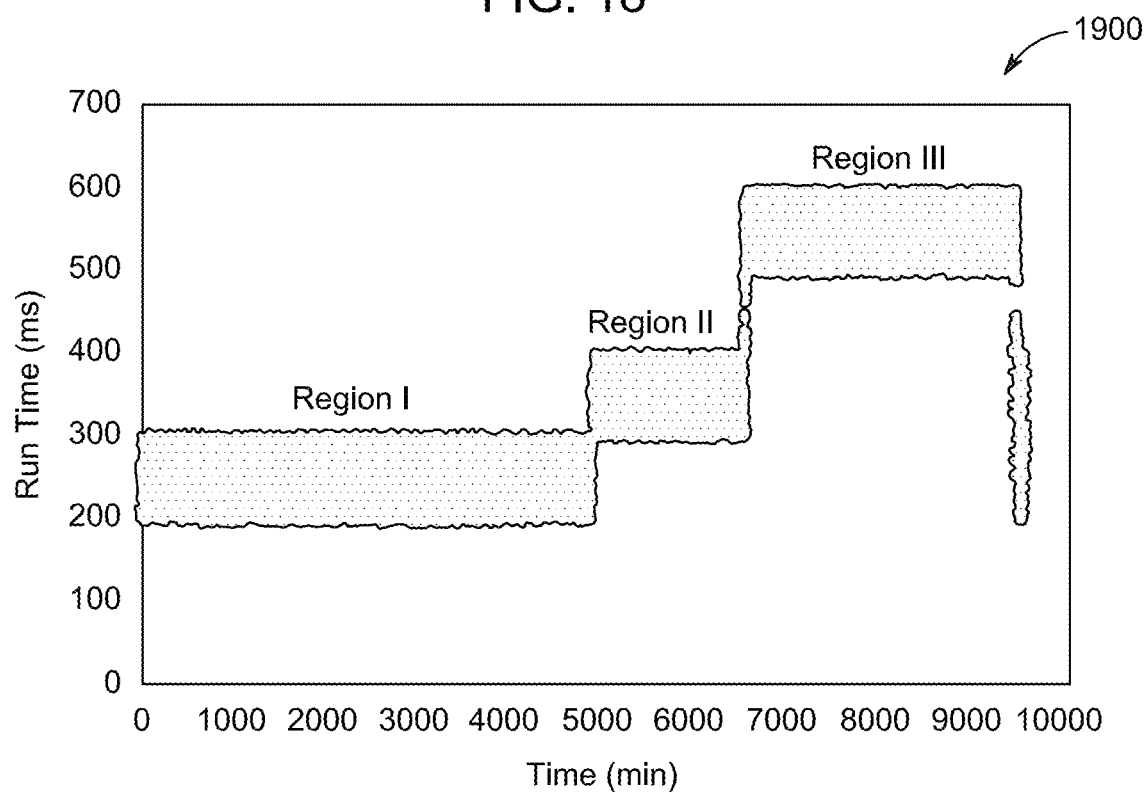
FIG. 19 is the ball run time plot for the MEG CDQs inhibition 2 experiment, according to certain embodiments.
Figure 20:
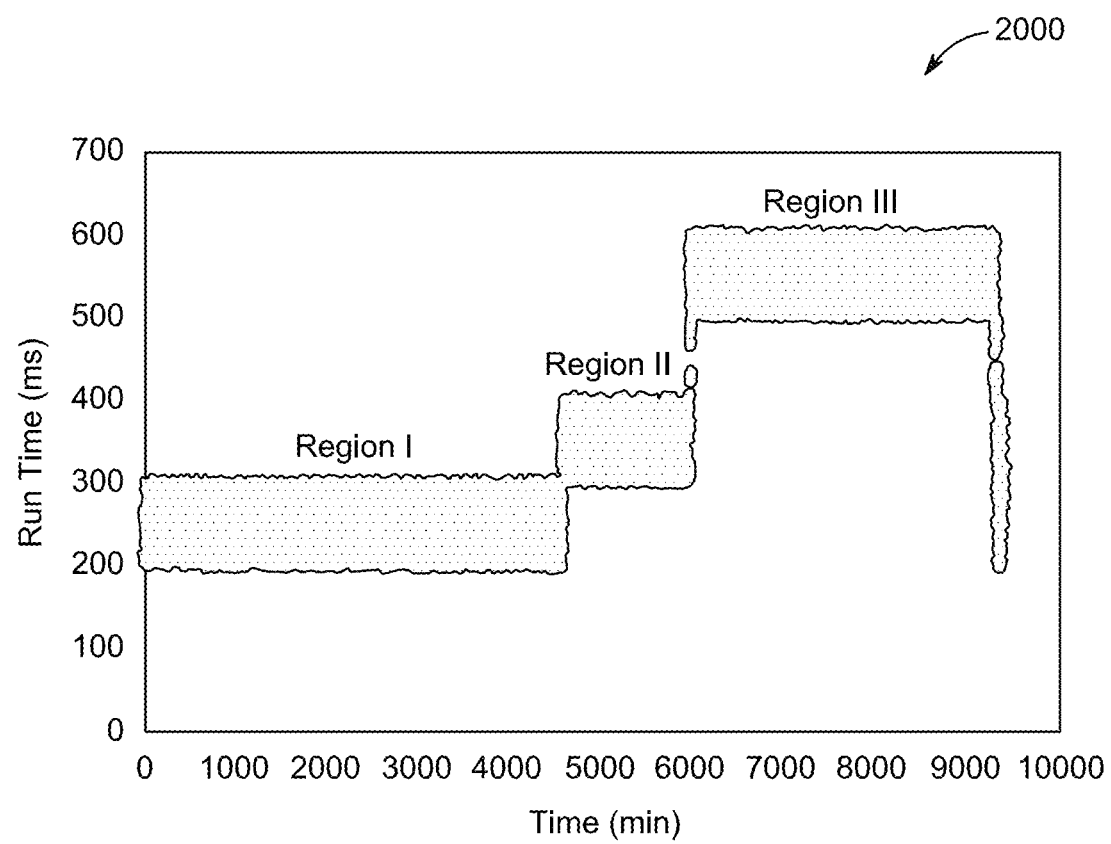
FIG. 20 is the ball run time plot for the MEG CDQs inhibition 3 experiment, according to certain embodiments.

In the MEG CQD inhibition 1 experiment, similar to the MEG inhibition 1 and 2 experiments, 200-300 minutes ball run time was maintained in the region I. The increase in the ball run time was limited to 400 and 600 minutes in region II and region III, respectively (FIG. 18—plot 1800). A decrease in ball run time for the MEG inhibition 1 and 2 experiments represents the retarded growth of hydrate crystals in the experimental solution and the anti-agglomerant characteristics of the MEG CQD. The same result was verified visually as the hydrate crystals remain in the slurry form (as shown in FIG. 14B). Similar behavior was seen in MEG CQD inhibition 2 and 3 experiments (as shown in FIGS. 19—plot 1900 and 20—plot 2000).

The hydrothermal method was effective in the preparation of the MEG CQDs. The prepared MEG CQDs decrease the gas hydrate induction temperature, increase the induction time, reduce the volumetric gas uptake, and provide excellent anti-agglomeration characteristics. Hence, a lower concentration of the MEG CQDs, in comparison to the MEG, can shift the hydrate equilibrium conditions toward higher pressure and lower temperature. The MEG CQDs, as prepared by the process of the present disclosure, may be used effectively at lower concentrations to prevent the $CO_2$ hydrate formation at any particular temperature and pressure range. The improved hydrate equilibrium conditions may positively affect economic and environmental issues associated with the $CO_2$ hydrate inhibition. The MEG CQDs include an increase in induction time and retardation of the hydrate crystal growth. The enhanced performance of the MEG CQDs may be attributed to the rise in the surface area of the MEG CQDs or to lower molecular weight.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method of inhibiting carbon dioxide ($CO_2$) hydrate formation in a $CO_2$ pipeline, comprising:
   injecting a composition comprising monoethylene glycol carbon quantum dots (MEG CQDs) into the $CO_2$ pipeline to deposit the MEG CQDs on an inside surface of the $CO_2$ pipeline;
   pressurizing the $CO_2$ pipeline with a gas stream containing $CO_2$ and water vapor at a pressure of 200-2,000 pounds per square inch (psi);
   wherein the MEG CQDs are present on the inside surface of the $CO_2$ pipeline in an amount effective to reduce the formation of $CO_2$ hydrates in the $CO_2$ pipeline during the pressurizing in comparison to the formation of the $CO_2$ hydrates in the $CO_2$ pipeline under the same conditions but in the absence of the MEG CQDs.

2. The method of claim 1, wherein the MEG CQDs have:
   an average size of 1-10 nanometer (nm);
   a substantially spherical shape; and
   a substantially crystalline structure.

3. The method of claim 1, wherein the MEG CQDs have:
   a fluorescence emission at 320-420 nm after excitation with light at 280-370 nm.

4. The method of claim 1, wherein the MEG CQDs are made by a method comprising:
   heating MEG to a temperature of 150-200 degree Celsius (° C.) for 20-30 hours to form a reaction solution; and
   centrifuging and filtering the reaction solution to separate the MEG CQDs.

5. The method of claim 1, wherein:
   the pressure during the pressurizing is 300-1000 psi.

6. The method of claim 1, wherein:
   the pressure during the pressurizing is 400-600 psi.

7. The method of claim 1, wherein:
   temperature of the inside surface of the $CO_2$ pipeline on which the MEG CQDs are deposited is 0-20° C. when pressurizing the $CO_2$ pipeline.

8. The method of claim 5, wherein:
   inhibition of the $CO_2$ hydrate formation is maintained above 4° C. when pressurizing the $CO_2$ pipeline.

9. The method of claim 1, wherein:
   inhibition of the $CO_2$ hydrate formation is maintained during the pressurizing for at least 4,000 minutes.

10. The method of claim 1, wherein:
    the MEG CQDs prevent agglomeration of the $CO_2$ hydrates in the $CO_2$ pipeline.

11. The method of claim 1, wherein:
    the gas stream contains 3-7 volume % (v %) water based on the total volume of the gas stream.

12. The method of claim 11, wherein:
    the amount effective of the MEG CQDs to reduce the formation of the $CO_2$ hydrates is 10-15 v % of the volume of water in the gas stream.

13. The method of claim 1, wherein the gas stream contains:
    80-95 v % $CO_2$;
    3-7 v % water;
    0.1-2 v % nitrogen gas;

0-1 v % of at least one hydrocarbon;
  wherein the hydrocarbon is selected from a group consisting of methane, ethane, propane, n-butane, iso-butane, n-pentane, and iso-pentane;
0-1 v % sulfur dioxide; and
0-1 v % of at least one nitrogen oxide (NOX) gas, based on the total volume of the gas stream.

14. The method of claim 1, wherein:
the $CO_2$ pipeline connects a $CO_2$ emission source and a geological formation; and
the gas stream is injected into the geological formation for $CO_2$ sequestration.

15. The method of claim 14, wherein:
the geological formation is a depleted oil reservoir, a depleted gas reservoir, a saline formation, or an unminable coal bed.

16. The method of claim 1, wherein:
the $CO_2$ pipeline connects a $CO_2$ source and an oil and/or gas reservoir; and
the gas stream is injected into the oil and/or gas reservoir for enhanced oil and/or gas recovery.

* * * * *